(12) United States Patent
Thompson

(10) Patent No.: US 6,852,535 B1
(45) Date of Patent: Feb. 8, 2005

(54) POLYMERASE III-BASED EXPRESSION OF THERAPEUTIC RNAS

(75) Inventor: James D. Thompson, Boulder, CO (US)

(73) Assignee: Sirna Therapeutics, Inc., Boulder, CO (US)

(*) Notice: Subject to any disclaimer, the term of this patent is extended or adjusted under 35 U.S.C. 154(b) by 0 days.

(21) Appl. No.: 09/630,846

(22) Filed: Aug. 2, 2000

Related U.S. Application Data

(63) Continuation of application No. 08/512,861, filed on Aug. 7, 1995, now Pat. No. 6,146,886, and a continuation-in-part of application No. 08/337,608, filed on Nov. 10, 1994, now Pat. No. 5,902,880, which is a continuation-in-part of application No. 08/293,520, filed on Aug. 19, 1994, now abandoned.

(51) Int. Cl.[7] .................. C07H 21/04; C12N 15/85; C12N 15/86; C12Q 1/68

(52) U.S. Cl. .................. 435/375; 435/6; 435/325; 536/24.5; 536/24.3; 536/24.31; 536/24.33

(58) Field of Search .................. 514/44; 435/325, 435/375, 91.1, 93.1; 536/23.1, 232, 24.5, 24.3, 24.31, 24.33

(56) References Cited

U.S. PATENT DOCUMENTS

| | | | |
|---|---|---|---|
| 5,208,149 A | * | 5/1993 | Inouye |
| 5,324,643 A | | 6/1994 | Greatbatch et al. |
| 5,624,803 A | * | 4/1997 | Noonberg et al. |
| 5,902,880 A | * | 5/1999 | Thompson |
| 6,146,886 A | * | 11/2000 | Thompson |

FOREIGN PATENT DOCUMENTS

| | | |
|---|---|---|
| WO | WO 89/11539 | 11/1989 |
| WO | WO 90/13641 | 11/1990 |
| WO | WO 92/07065 | 4/1992 |
| WO | WO 93/11253 | 6/1993 |
| WO | WO 93/23057 | 11/1993 |
| WO | WO 93/23569 | 11/1993 |
| WO | WO 94/02495 | 2/1994 |
| WO | WO 94/16736 | 8/1994 |
| WO | WO 94/24983 | 11/1994 |
| WO | WO 94/29452 | 12/1994 |

OTHER PUBLICATIONS

Verma et al, Gene therapy—promises, problems and prospects, Sep. 1997, Nature, vol. 389, pp. 239–242.*
W. French Anderson, Human Gene Therapy, Apr. 1998, Nature, vol. 392, pp. 25–30.*
Orkin et al, Report and recommendations of the panel to assess the NIH investment in research on gene therapy, Dec. 1995, NIH, pp. 1–31.*

(List continued on next page.)

Primary Examiner—Karen A. Lacourciere
(74) Attorney, Agent, or Firm—McDonnell Boehnen Hulbert & Berghoff LLP

(57) ABSTRACT

A transcribed non-naturally occurring RNA molecule comprising a desired RNA molecule, wherein the 3' region of the RNA is able to base-pair with at least 8 bases at the 5' terminus of the same RNA molecule.

13 Claims, 32 Drawing Sheets

OTHER PUBLICATIONS

Ellington et al. In vitro selection of RNA molecules that bind specific ligands. Nature. vol. 346, Aug. 30, 1990, pp. 818–882.*

Cameron and Jennings, "Specific Gene Expression by Engineered Ribozymes in Monkey Cells," Proc. Natl. Acad. Sci. USA 86:9139–9143 (1989).

Cushman et al., 1996, "Ribozyme Inhibition of VEGF–Mediated Endothelial Cell Proliferation in Cell Culture and VEGF–Induced Angiogenesis in a Rat Corneal Model" Abstract in IBC USA Conferences—Angiogenesis Inhibitors.

Desjardins et al., "Pharmacokinetics of a Synthetic, Chemically Modified Hammerhead Ribozyme Against the Rat Cytochrome P–450 3A2 Mrna After Single Intravenous Injections," J. Pharmacology and Experimental Therapeutics 27(8):1419–1427 (1996).

Efrat et al., "Ribozyme–mediated attenuation of pancreatic β–cell glucokinase expression in transgenic mice results in impaired glucose–induced insulin secretion," Proc. Natl. Acad. Sci. USA 91:2051–2055 (1994).

Flory et al., "Nuclease–resistant ribozymes decrease stromelysin mRNA levels in rabbit synovium following exogenous delivery to the knee joint," Proc. Natl. Acad. Sci. USA 93:754–758 (1996).

Larsson et al., "Reduced β2–microglobulin mRNA levels in transgenic mice expressing a designed hammerhead ribozyme," Nucleic Acids Research 22(12):2242–2248 (1994).

Lieber and Kay, "Adenovirus–Mediated Expression of Ribozymes in Mice," Journal of Virology 70(5):3153–3158 (1996).

Lyngstadaas et al., "A synthetic, chemically modified ribozyme eliminates amelogenin, the major translation product in developing mouse enamel in vivo," EMBO J. 14:5224–5229 (1995).

Malone et al., "Cationic liposome–mediated RNA transfection", Proc. Nat. Acad. Sci. USA 86:6077 (1989).

RPI Press Release, Aug. 29, 2001, http://www.prnewswire.com/cgi–bin/micro_stories.pl?ACCT=742975&TICK=RZYM&STORY=/www/story/08–29–2001/0001562763&EDATE=Aug+29,+2001.

RPI Press Release, Jun. 20, 2001, http://www.prnewswire.com/cgi–bin/micro_stories.pl?ACCT=742975&TICK=RZYM&STORY=/www/story/06–20–2001/0001517763&EDATE=Jun+20,+2001.

RPI Press Release, Oct. 8, 2001, http://www.prnewswire.com/cgi–bin/micro_stories.p1?ACCT=742975&TICK=RZYM&STORY=/www/story/10–08–2001/0001586793&EDATE=Oct+8,+2001.

Sambrook et al. (Molecular Cloning, A Laboratory Manual, 2nd ed., 1989, sections 16.30–.32).

Seachrist, Bioworld Today, Jan. 15, 1997, at http:www.bioworld.com/bw/static.htm?path=br/data/bt01151997/bt01151997e.html.

Sioud, "Ribozyme modulation of lipopolysaccharide–induced tumor necrosis factor–α production by peritoneal cells in vitro and in vivo," Eur. J. Immunol. 26:1026–1031 (1996).

Uhlmann and Peyman, "Antisense Oligonucleotides: A New Therapeutic Principle," Chemical Reviews 90:544–584 (1990).

Yamamoto et al., "Abrogation of Lung Metastasis of Human Fibrosarcoma Cells by Ribozyme–Mediated Suppression of Integrin α6 Subunit Expression," Int. J. Cancer 65:519–524 (1996).

Adeniyi–Jones et al., "Generation of long read– through transcripts in vivo and in vitro by deletion 3' termination and processing sequences in the human tRNAimet gene," Nucleic Acids Research 12:1101–1115 (1984).

Ashom et al., "Elimination of infectious human immunodeficiency virus from human T–cell cultures by synergistic action of CD4–Pseudomonas exotoxin and reverse transcriptase inhibitors," Proc. Natl. Acad. Sci. USA 87:8889–8893 (1990).

Ballantyne et al., "Nucleotide sequence of the cDNA for murine intercellular adhesion molecule–1 (ICAM–1)," Nucleic Acids Research 17:5853 (1989).

Bahner et al., "Comparison of trans–Dominant Inhibitory Mutant Human Immunodeficiency Virus Type 1 Genes Expressed by Retroviral Vectors in Human T–Lymphocytess," J. Virology 67:3199–3207 (1993).

Baltimore, "Intracellular Immunization," Nature 335:395–396 (1988).

Barinaga, "Ribozymes: Killing the Messenger," Science 262:1512–1514 (1993).

Berkner, "Development of Adenovirus Vectors for the Expression of Heterologous Genes," BioTechniques 6:616–629 (1988).

Bredow et al., "Sequence and factor requirements for faithful in vitro transcription of human 7SL DNA," Gene 86:217–225 (1990).

Carter, Curr. Opin. Genet. Dev. 3:74 (1992).

Cech, "Ribozymes and Their Medical Implications," JAMA 260:3030–3034 (1988).

Chomcyzynski and Sacchi, "Single Step Method of RNA Isolation by Acid Guanidinum Thiocyanate–Phenol–Chloroform Extraction," Analytical Biochem. 162:156–159 (1987).

Cotten and Birnstiel, "Ribozyme Mediated Destruction of RNA in vivo," EBMO J 8:3861–3865 (1989).

Cotten, "The in vivo application of ribozymes," TIBTECH 8:174–178 (1990).

Edgington, "Ribozymes: Stop Making Sense," Biotechnology 10:256–262 (1992).

Eguchi et al., "Antisense RNA," Annu. Rev. Biochem. 60:631–652 (1991).

Fowlkes and Shenk, "Transcriptional Control Regions of the Adenovirus VAI RNA Gene," Cell 22:405–413 (1980).

Geiduschek and Tocchini–Valentini, "Transcription by RNA Polymerase III," Ann. Rev. Biochem. 57:873–914 (1988).

Gupta and Reddy, "Compilation of small RNA sequences," Acids Research 19 (Supplement):2073–2075 (1991).

Hall et al., "Transcription Initiation of Eucaryotic Transfer RNA Genes," Cell 29:3–5 (1982).

Howe and Shu, "Epstein–Barr Virus Small RNA (EBER) Genes: Unique Transcription Units That Combine RNA Polymerase II and III Promoter Elements," Cell 57:825–834 (1989).

Kickhoefer et al., "Vault Ribonucleoprotein Particles from Rat and Bullfrog Contain a Related Small RNA That Is Transcribed by RNA Polymerase III," J. Biol. Chem. 268:7868–7873 (1993).

Kita et al., "Sequence and expression of rat ICAM–1," Biochem. Biophys. Acta 1131:108–110 (1992).

Lee et al., "Transcription of Xenopus Selenocysteine tRNASer (Formerly Designated Opal Suppressor Phosphoserine tRNA) Gene Is Directed by Mutible 5'–Extragenic Regulatory Elements," J. Biol. Chem. 264:9696–9702 (1989).

Lee et al., "Overexpression of RRE–Derived Sequences Inhibits HIV–1 Replication in CEM Cells," The New Biologist 4:66–74 (1992).

Lieber and Strauss, Selection of Efficient Cleavage Sites in Target RNAs by Using a Ribozyme Expression Library, Mol. Cellular Biol. 15:540–551 (1995).

Malim et al., "Functional Comparison of the Rev Trans–activators Encoded by Different Primate Immunodeficiency Virus Species" Proc. Natl. Acad. Sci. USA 86:8222–8226 (1989).

Mattaj et al., "Changing the RNA Polymerase Specificity of U snRNA Gene Promoters," Cell 55:435–442 (1988).

Nielsen et al., "Transcription of Human 5S rRNA Genes is Influenced by an Upstream DNA Sequence," Nucleic Acids Research 21:3631–3636 (1993).

Romero and Blackburn, "A Conserved Secondary Structure for Telomerase RNA," Cell 67:343–353 (1991).

Sarver and Rossi, "Gene Therapy: A Bold Direction for HIV–1 Treatment," Aids Research and Human Retroviruses 9:483–487 (1993).

Simons et al., "ICAM, an adhesion ligang of LFA–1, is homologous to the neutral cell adhesion molecule NCAM," Nature 331:624–627 (1988).

Specht et al., "Compilation of 5S rRNA and 5S rRNA gene sequences," Nucleic Acids Research 19 Supplement 2189–2191 (1991).

Sullenger et al., "Overexpression of TAR Sequences Renders Cells Resistant to Human Immunodeficiency Virus Replication," Cell 63:601–608 (1990).

Sullenger et al., "Expression of Chimeric tRNA–Driven Antisense Transcipts Renders NIH 3T3 Cells Highly Resistant to Moloney Murine Leukemia Virus Replication," Molecular and Cellular Biology 10:6512–6523 (1990).

Sullenger et al., "Analysis of trans–Acting Response Decoyo RNA–Mediated Inhibition of Human Immunodeficiency Virus Type 1 Transactivation," J. Virology 65:6811–6816 (1991).

Tsai et al., "In vitro selection of an RNA epitope immunologically cross–reactive with a peptide," Proc. Natl. Acad. Sci. USA 89:8864–8868 (1992).

Usman and Cedergren, "Exploiting the chemical synthesis of RNA," TIBS 17:334–339 (1992).

Vickers et al., "Inhibition of HIV–LTR gene expression by oligonucleotides targeted to the TAR element," Nucleic Acids Research 19:3359–3368 (1991).

Willis, "RNA Polymerase III Genes, factors and transcriptional specificity," Biochemistry 212:1–11 (1993).

Wincott et al., "Synthesis, deprotection, analysis and purification of RNA and ribozymes," Nucleic Acids Research 23(14):2677–2684 (1995).

Yu et al., "A Hairpin Ribozyme Inhibits Expression of Diverse Strains of Human Immunodeficiency Virus Type 1," Proc. Natl. Acad. Sci. USA 90:6340–6344 (1993).

* cited by examiner

Variants of Δ3-5 RNA

S35 tRNA Chimera (S35)

S35 Ribozyme Chimera (HHIS35)

S35 Sequence

GGCAGAACAG CAGAGUGGCG CAGCGGAAGC GUGCUGGGCC CAUAACCCAG  50

AGGUCGAUGG AUCGAAACCC CGGAUCGUAC CGCGGUGGAU CCACUCUGCU  100

GUUCUGUUU  109

FIGURE 11 a

HHIS35

GGCAGAACAG CAGAGUGGCG CAGCGGAAGC GUGCUGGGCC CAUAACCCAG 50

AGGUCGAUGG AUCGAAACCC CGGAUCGUAC CGCGG<u>CACAA</u> <u>CACUGAUGAG</u> 100

<u>GACCGAAAGG</u> <u>UCCGAAACGG</u> <u>GCA</u>GGAUCCA CUCUGCUGUU CUGUUU 146

Underlined bases indicate the HHI ribozyme sequence

FIGURE 11 b

S35 Plus Sequence

GGCAGAACAG CAGAGUGGCG CAGCGGAAGC GUGCUGGGCC CAUAACCCAG    50

AGGUCGAUGG AUCGAAACCC CGGAUCGUAC CGCGGGGAUC CUAACGAUCC    100

GGGGUGUCGA UCCAUCACUC UGCUGUUCUG UU U    133

FIGURE 12 a

HHIS35 Plus

GGCAGAACAG CAGAGUGGCG CAGCGGAAGC GUGCUGGGCC CAUAACCCAG  50

AGGUCGAUGG AUCGAAACCC CGGAUCGUAC CGCGG<u>CACAA CACUGAUGAG</u>  100

<u>GACCGAAAGG UCCGAAACGG GCA</u>GGAUCCU AACGAUCCGG GGUGUCGAUC  150

CAUCACUCUG CUGUUCUGUU U  171

Underlined bases indicate the HHI ribozyme sequence

FIGURE 12 b

Proposed Chemical Formula for S35 Expression Cassette

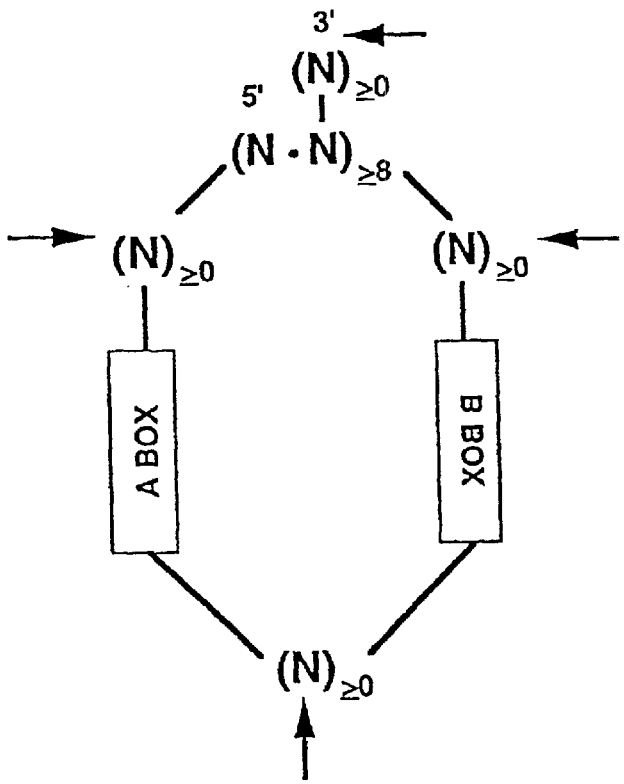

A BOX = URGCNNAGYGG

B BOX = GGUUCGANUCC

This is based on Geiduschek & Tocchini-Valentini, (1988) Annu. Review Biochem. 57, 873-914. However this consensus sequence is not meant to be limiting N = A, U, G, or C R = Purine Y = Pyrimidine

• = Indicates base-pairing

— = Indicates covalent linkage

➤ = Indicates sites at which desired RNAs can be cloned

FIGURE 13

5T tRNA Chimera Construct

5T Ribozyme Chimera (HHI5T)

5T tRNA Chimera (5T)

5T Ribozyme Chimera (HHI5T)

TRZ-RNA Chimeras
A: TRZ-A
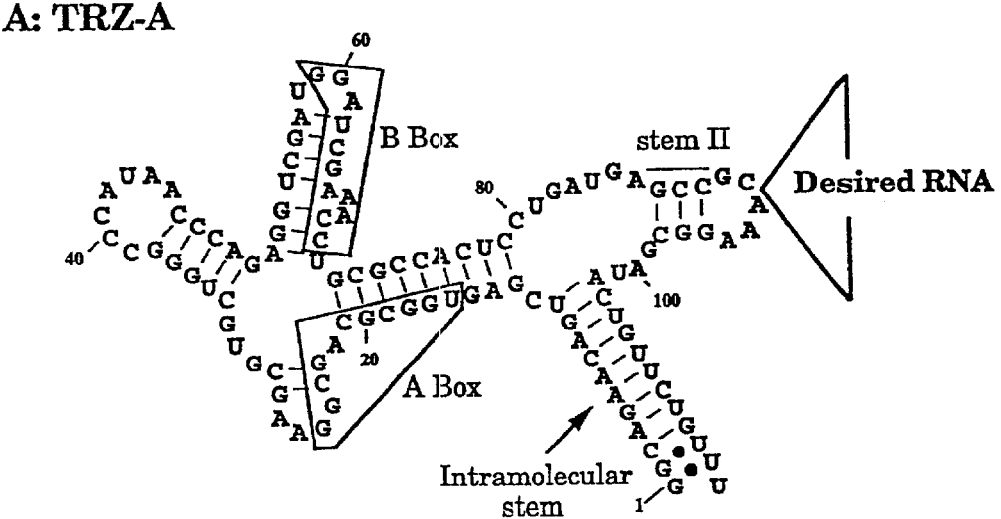
B: TRZ-B
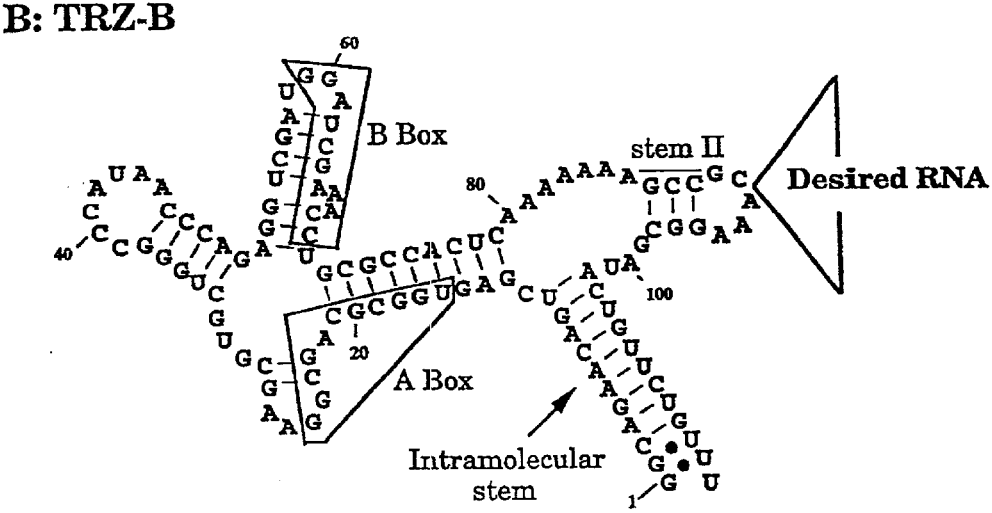
Figure 16

HHITRZ-A Ribozyme Chimera

HPITRZ-A Ribozyme Chimera

Figure 19: U6 -S35 Chimera
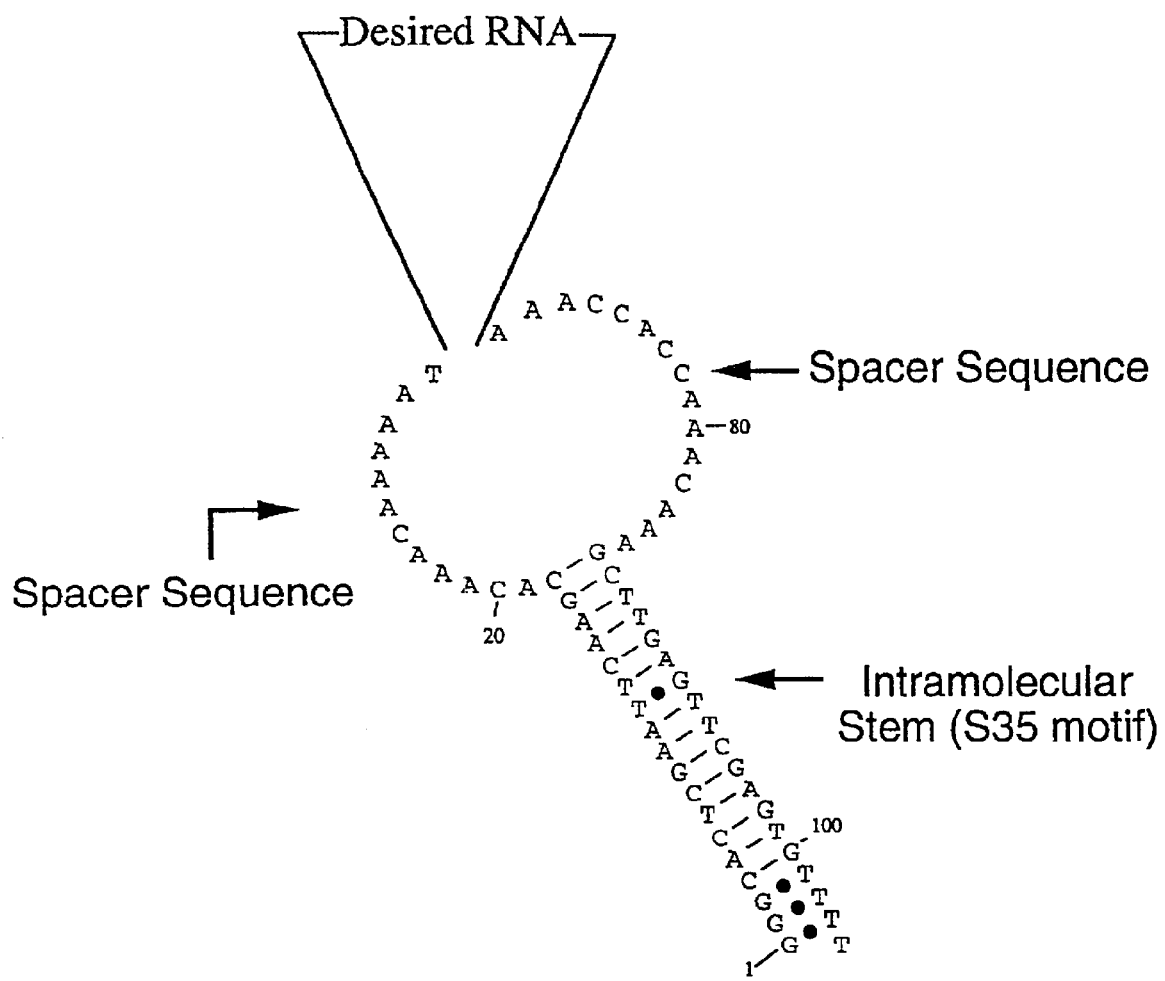

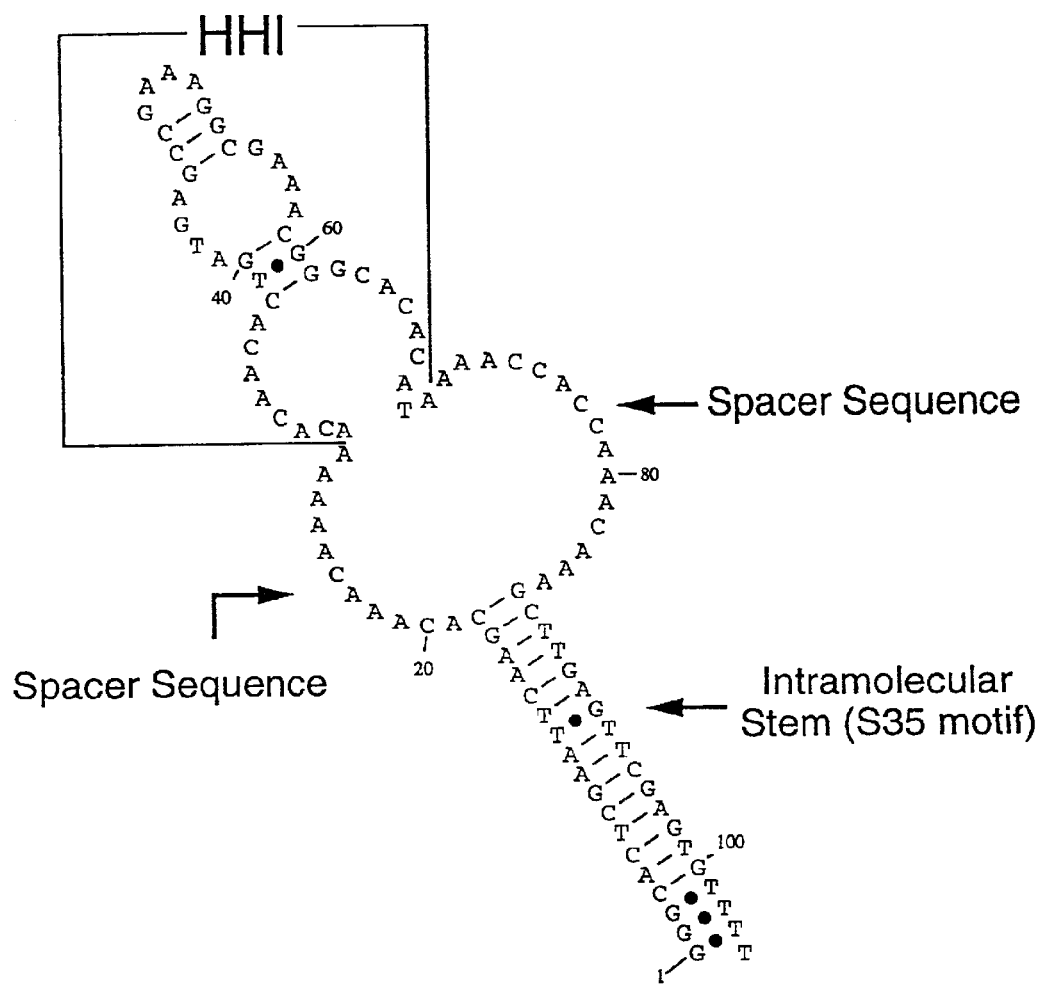
Figure 20: Human U6-S35-Ribozyme Chimera (U6-S35-HHI)

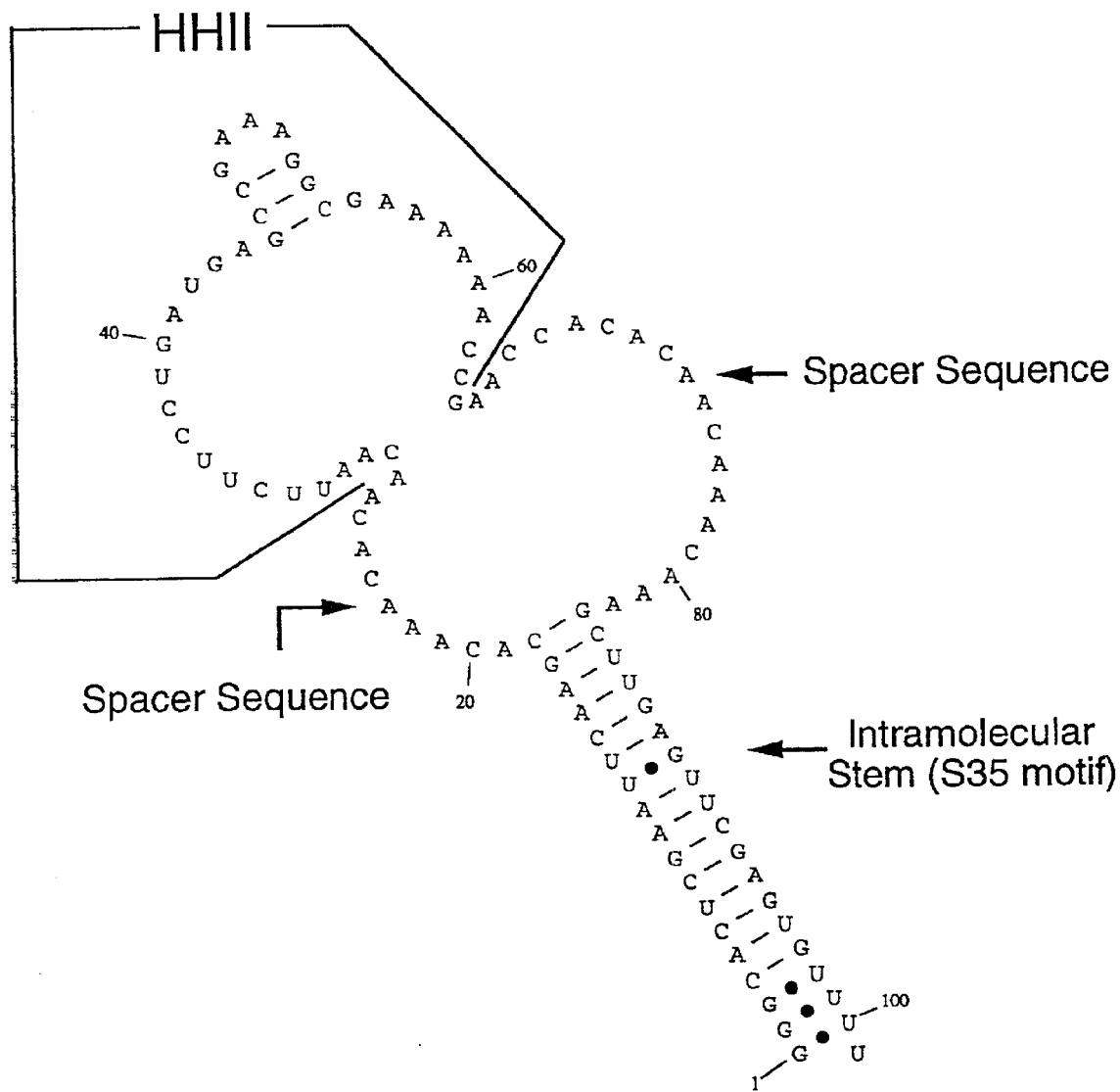
Figure 21: Human U6-S35-Ribozyme Chimera (U6C-S35-HHII)

Figure 22: RNA Cleavage by U6-S35-Chimera
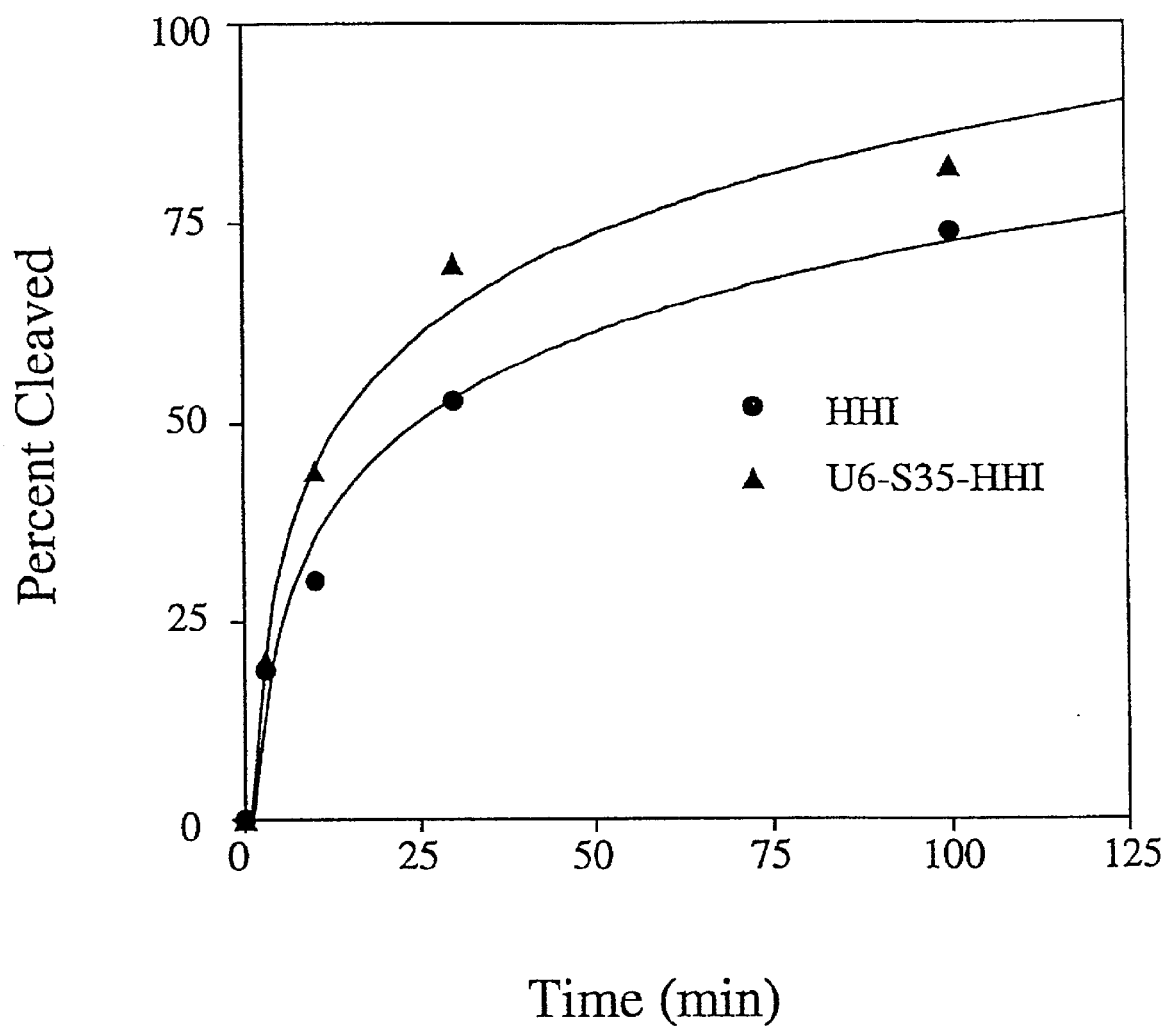

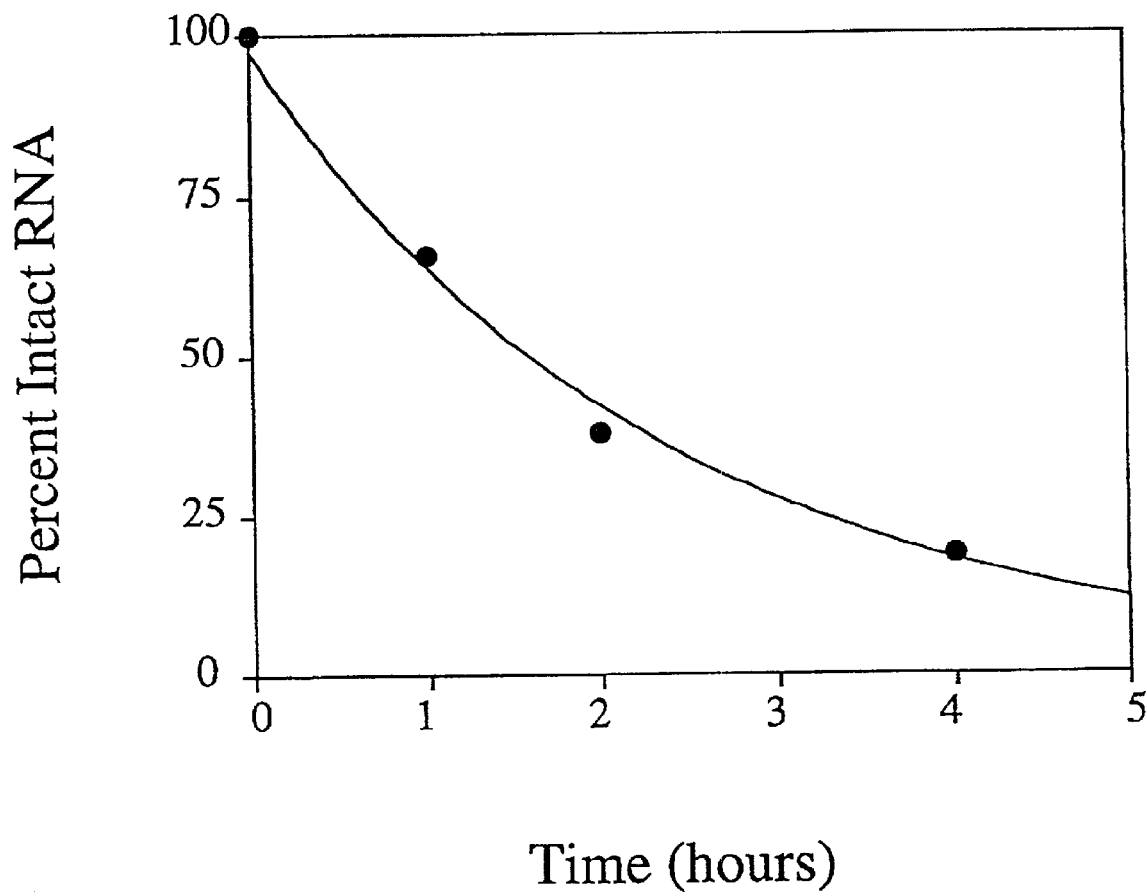
Figure 23: Stability of U6-S35-HHII RNA in Mammalian Cells

Figure 24: Adenovirus VA I RNA
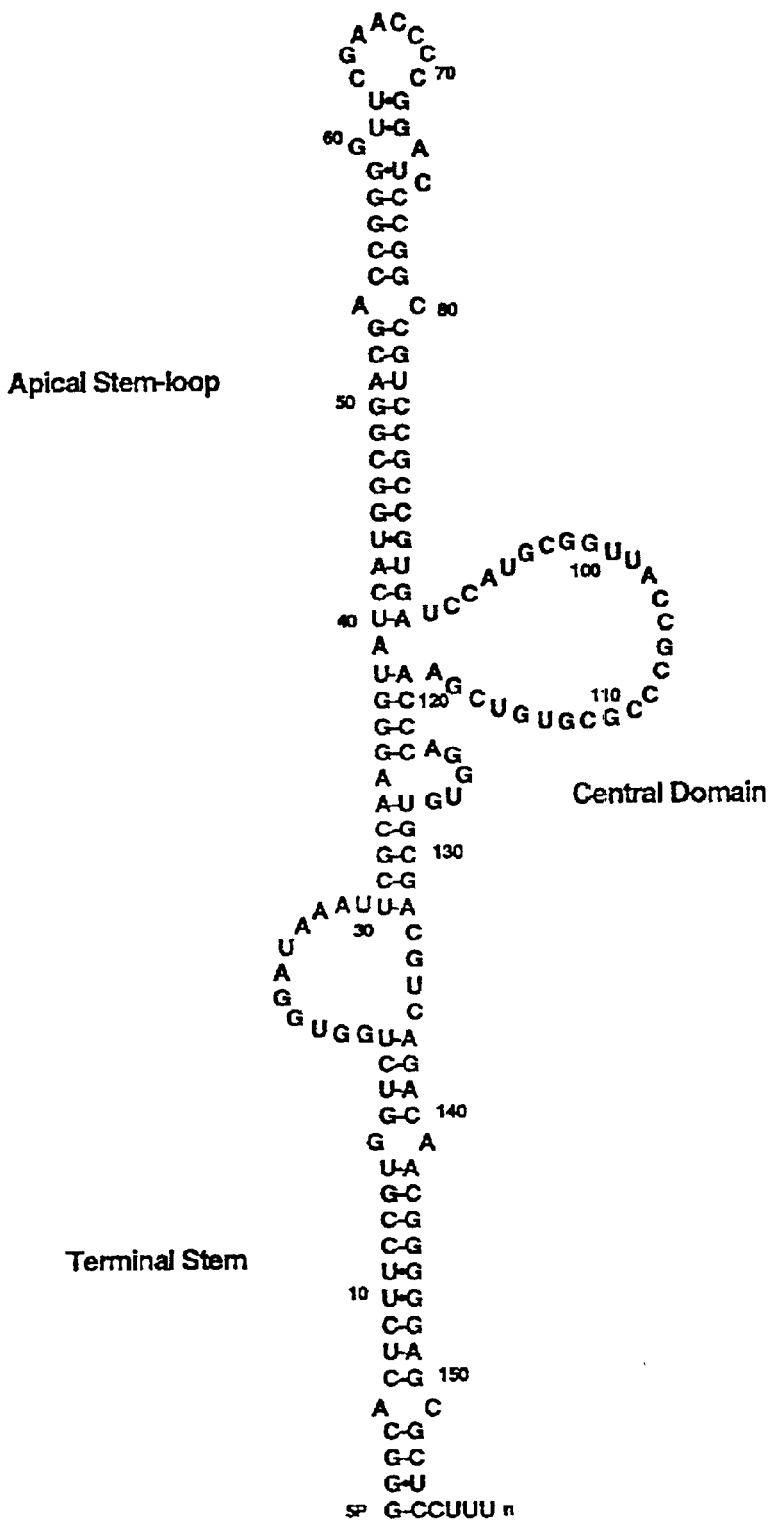

Figure 25: VA1-Chimers
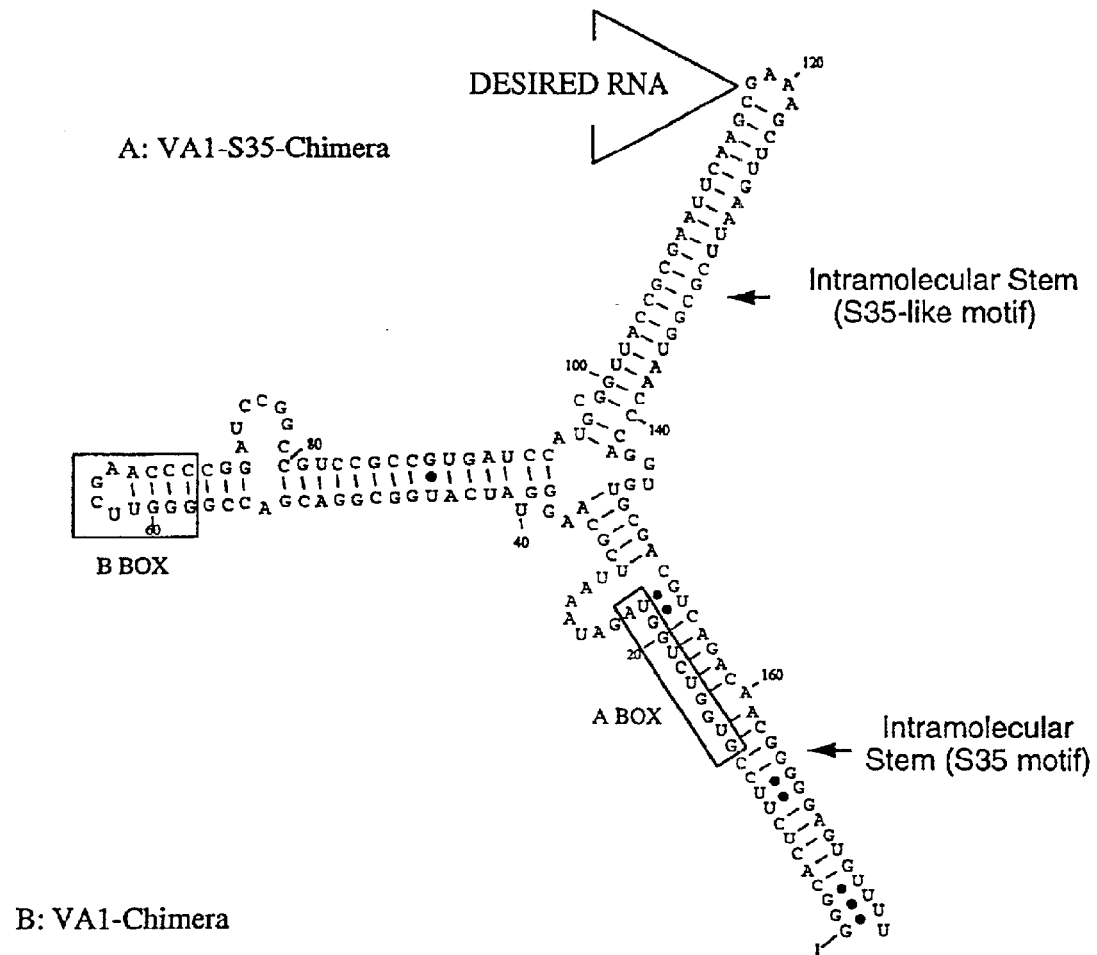
A: VA1-S35-Chimera
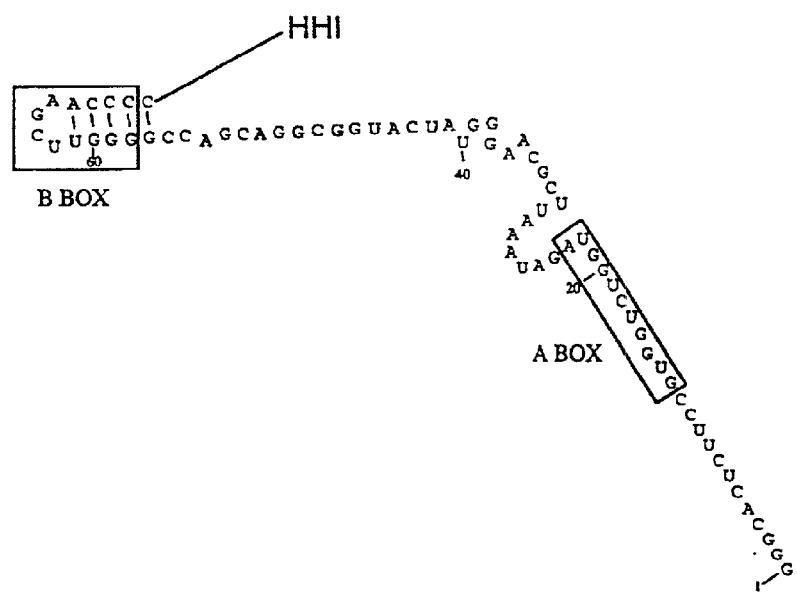
B: VA1-Chimera

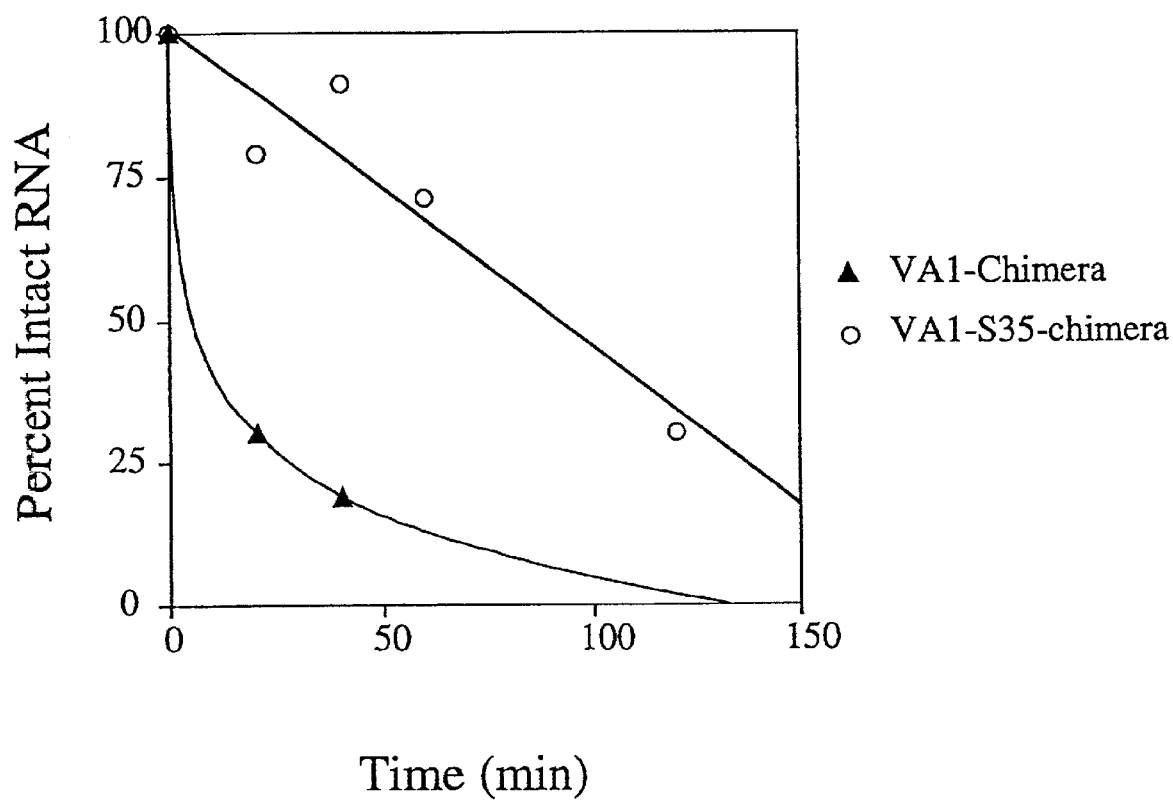
Figure 26: Stability of VA1-chimeric RNA in Mammalian Cells

POLYMERASE III-BASED EXPRESSION OF THERAPEUTIC RNAS

This application is a continuation of U.S. Ser. No. 08/512,861 by Thompson, entitled "Improved RNA Polymerase III-Based Expression of Therapeutic RNAs," filed Aug. 7, 1995, now U.S. Pat. No. 6,146,886 incorporated herein by reference in its entireity, including drawings, which is a continuation-in-part of James Thompson, "Improved RNA Polymerase III-Based Expression of Therapeutic RNAS", U.S. Ser. No. 08/293,520, filed Aug. 19, 1994 now abandoned, and James Thompson, "Improved RNA Polymerase III-Based Expression of Therapeutic RNAS", U.S. Ser. No. 08/337,608, filed Nov. 10, 1994, now U.S. Pat. No. 5,902,880 hereby incorporated by reference herein.

BACKGROUND OF THE INVENTION

This invention relates to RNA polymerase III-based methods and systems for expression of therapeutic RNAs in cells in vivo or in vitro.

The RNA polymerase III (pol III) promoter is one found in DNA encoding 5S, U6, adenovirus VA1, Vault, telomerase RNA, tRNA genes, etc., and is transcribed by RNA polymerase III (for a review see Geiduschek and Tocchini-Valentini, 1988 *Annu. Rev. Biochem.* 57, 873–914; Willis, 1993 *Eur. J. Biochem.* 212, 1–11). There are three major types of pol III promoters: types 1, 2 and 3 (Geiduschek and Tocchini-Valentini, 1988 supra; Willis, 1993 supra) (see FIG. 1). Type 1 pol III promoter consists of three cis-acting sequence elements downstream of the transcriptional start site a) 5' sequence element (A block); b) an intermediate sequence element (I block); c) 3' sequence element (C block). 5S ribosomal RNA genes are transcribed using the type 1 pol III promoter (Specht et al., 1991 *Nucleic Acids Res.* 19, 2189–2191.

The type 2 pol III promoter is characterized by the presence of two cis-acting sequence elements downstream of the transcription start site. All Transfer RNA (tRNA), adenovirus VA RNA and Vault RNA (Kikhoefer et al., 1993, *J. Biol. Chem.* 268, 7868–7873) genes are transcribed using this promoter (Geiduschek and Tocchini-Valentini, 1988 supra; Willis, 1993 supra). The sequence composition and orientation of the two cis-acting sequence elements-A box (5' sequence element) and B box (3' sequence element) are essential for optimal transcription by RNA polymerase III.

The type 3 pol III promoter contains all of the cis-acting promoter elements upstream of the transcription start site. Upstream sequence elements include a traditional TATA box (Mattaj et al., 1988 Cell 55, 435–442), proximal sequence element (PSE) and a distal sequence element (DSE; Gupta and Reddy, 1991 *Nucleic Acids Res.* 19, 2073–2075). Examples of genes under the control of the type 3 pol III promoter are U6 small nuclear RNA (U6 snRNA) and Telomerase RNA genes.

In addition to the three predominant types of pol III promoters described above, several other pol III promoter elements have been reported (Willis, 1993 supra) (see FIG. 1). Epstein-Barr-virus-encoded RNAs (EBER), *Xenopus* seleno-cysteine tRNA and human 7SL RNA are examples of genes that are under the control of pol III promoters distinct from the aforementioned types of promoters. EBER genes contain a functional A and B box (similar to type 2 pol III promoter). In addition they also require an EBER-specific TATA box and binding sites for ATF transcription factors (Howe and Shu, 1989 *Cell* 57,825–834). The seleno-cysteine tRNA gene contains a TATA box, PSE and DSE (similar to type 3 pol III promoter). Unlike most tRNA genes, the seleno-cysteine tRNA gene lacks a functional A box sequence element. It does require a functional B box (Lee et al., 1989 *J. Biol. Chem.* 264, 9696–9702). The human 7SL RNA gene contains an unique sequence element downstream of the transcriptional start site. Additionally, upstream of the transcriptional start site, the 7SL gene contains binding sites for ATF class of transcription factors and a DSE (Bredow et al., 1989 Gene 86, 217–225).

Gilboa WO 89/11539 and Gilboa and Sullenger WO 90/13641 describe transformation of eucaryotic cells with DNA under the control of a pol III promoter. They state:

"In an attempt to improve antisense RNA synthesis using stable gene transfer protocols, the use of pol III promoters to drive the expression of antisense RNA can be considered. The underlying rationale for the use of pol III promoters is that they can generate substantially higher levels of RNA transcripts in cells as compared to pol II promoters. For example, it is estimated that in a eucaryotic cell there are about $6 \times 10^7$ t-RNA molecules and $7 \times 10^5$ mRNA molecules, i.e., about 100 fold more pol III transcripts of this class than total pol II transcripts. Since there are about 100 active t-RNA genes per cell, each t-RNA gene will generate on the average RNA transcripts equal in number to total pol II transcripts. Since an abundant pol II gene transcript represents about 1% of total mRNA while an average pol II transcript represents about 0.01% of total mRNA, a t-RNA (pol III) based transcriptional unit may be able to generate 100 fold to 10,000 fold more RNA than a pot II based transcriptional unit. Several reports have described the use of pol III promoters to express RNA in eucaryotic cells. Lewis and Manley and Sisodia have fused the Adenovirus VA-1 promoter to various DNA sequences (the herpes TK gene, globin and tubulin) and used transfection protocols to transfer the resulting DNA constructs Into cultured cells which resulted in transient synthesis of RNA in the transduced cell. De la Pena and Zasloff have expressed a t-RNA-Herpes TK fusion DNA construct upon microinjection into frog oocytes. Jennings and Molloy have constructed an antisense RNA template by fusing the VA-1 gene promoter to a DNA fragment derived from SV40 based vector which also resulted in transient expression of antisense RNA and limited inhibition of the target gene". [Citations omitted.]

The authors describe a fusion product of a chimeric tRNA and an RNA product (see FIG. 1C of WO 90/13641). In particular they describe a human tRNA met$_i$ derivative 3-5. 3-5 was derived from a cloned human tRNA gene by deleting 19 nucleotides from the 3' end of the gene. The authors indicate that the truncated gene can be transcribed if a termination signal is provided, but that no processing of the 3' end of the RNA transcript takes place.

Adeniyi-Jones et al., 1984 *Nucleic Acids Res.* 12, 1101–1115, describe certain constructions which "may serve as the basis for utilizing the tRNA gene as a 'portable promoter' in engineered genetic constructions." The authors describe the production of a so-called Δ3'-5 in which 11 nucleotides of the 3'-end of the mature tRNA$_i^{met}$ sequence are replaced by a plasmid sequence, and are not processed to generate a mature tRNA. The authors state:

the properties of the tRNA$_i^{met}$ 3' deletion plasmids described in this study suggest their potential use in certain engineered genetic constructions. The tRNA gene could be used to promote transcription of theoretically any DNA sequence fused to the 3' border of the gene, generating a fusion gene which would utilize the efficient polymerase III promoter of the human tRNA$_i$met gene. By fusion of the DNA sequence to a tRNA$_i$met deletion mutant such as Δ3'-4, a long read-through transcript would be generated in vivo (dependent, of course, on the absence of effective RNA polymerase III termination sequences). Fusion of the DNA sequence to a tRNA$_i$met deletion mutant such as Δ3'-5 would lead to the generation of a co-transcript from which subsequent processing of the tRNA leader at the 5' portion of the fused transcript would be blocked. Control over processing may be of some biological use in engineered constructions, as suggested by properties of mRNA species bearing tRNA sequences as 5' leaders in prokaryotes. Such "dual transcripts" code for several predominant bacterial proteins such as EF-Tu and may use the tRNA leaders as a means of stabilizing the transcript from degradation in vivo. The potential use of the tRNA$_i$met gene as a "promoter leader" in eukaryotic systems has been realized recently in our laboratory. Fusion genes consisting of the deleted tRNA$_i$met sequences contained on plasmids Δ 3'-4 and Δ 3'-5 in front of a promoter-less Herpes simplex type I thymidine kinase gene yield viral-specific enzyme resulting from RNA polymerase III dependent transcription in both X. Iaevis oocytes and somatic cells". [References omitted].

Sullenger et al., 1990 Cell 63, 601–619, describe overexpression of TAR-containing sequences using a chimeric tRNA$_i$met-TAR transcription unit in a double copy (DC) murine retroviral vector.

Sullenger et al., 1990 Molecular and Cellular Bio. 10, 6512, describe expression of chimeric tRNA driven antisense transcripts. It indicates:

successful use of a tRNA-driven antisense RNA transcription system was dependent on the use of a particular type of retroviral vector, the double-copy (DC) vector, in which the chimeric tRNA gene was inserted in the viral LTR. The use of an RNA pol III-based transcription system to stably express high levels of foreign RNA sequences in cells may have other important applications. Foremost, it may significantly improve the ability to inhibit endogenous genes in eucaryotic cells for the study of gene expression and function, whether antisense RNA, ribozymes, or competitors of sequence-specific binding factors are used. tRNA-driven transcription systems may be particularly useful for introducing "mutations" into the germ line, i.e., for generating transgenic animals or transgenic plants. Since tRNA genes are ubiquitously expressed in all cell types, the chimeric tRNA genes may be properly expressed in all tissues of the animal, in contrast to the more idiosyncratic behavior of RNA pol II-based transcription units. However, homologous recombination represents a more elegant although, at present, very cumbersome approach for introducing mutations into the germ line. In either case, the ability to generate transgenic animals or plants carrying defined mutations will be an extremely valuable experimental tool for studying gene function in a developmental context and for generating animal models for human genetic disorders. In addition, tRNA-driven gene inhibition strategies may also be useful in creating pathogen-resistant livestock and plants. [References omitted.]

Cotten and Birnstiel, 1989 EMBO Jrnl. 8, 3861, describe the use of tRNA genes to increase intracellular levels of ribozymes. The authors indicate that the ribozyme coding sequences were placed between the A and the B box internal promoter sequences of the Xenopus tRNA$^{met}$ gene. They also indicate that the targeted hammerhead ribozymes were active in vivo.

Yu et al., 1993 Proc. Natl. Acad. Sci. USA 90, 5340, describe the use of a VAI promoter to express a hairpin ribozyme. The resulting transcript consisted of the first 104 nucleotides of the VAI RNA, followed by the ribozyme sequence and the terminator sequence. Lieber and Strauss, 1995 Mol. Cellular Bio. 15, 540, inserted a hammerhead ribozyme sequence in the central domain of a VAI RNA.

SUMMARY OF THE INVENTION

Applicant has determined that the level of production of a foreign RNA, using a RNA polymerase III (pol III) based system, can be significantly enhanced by ensuring that the RNA is produced with the 5' terminus and a 3' region of the RNA molecule base-paired together to form a stable intramolecular stem structure. This stem structure is formed by hydrogen bond interactions (either Watson-Crick or non-Watson-Crick) between nucleotides in the 3' region (at least 8 bases) and complementary nucleotides in the 5' terminus of the same RNA molecule.

Although the example provided below involves a type 2 pol III gene unit, a number of other pol III promoter systems can also be used, for example, tRNA (Hall et al., 1982 Cell 29, 3-5), 5S RNA (Nielsen et al., 1993, Nucleic Acids Res. 21 3631–3636), adenovirus VA RNA (Fowlkes and Shenk, 1980 Cell 22,405–413), U6 snRNA (Gupta and Reddy, 1990 Nucleic Acids Res. 19, 2073–2075), vault RNA (Kickoefer et al., 1993 J. Biol. Chem. 268, 7868–7873), telomerase RNA (Romero and Blackburn, 1991 Cell 67, 343–353), and others.

The construct described in this invention is able to accumulate RNA to a significantly higher level than other constructs, even those in which 5' and 3' ends are involved in hairpin loops. Using such a construct the level of expression of a foreign RNA can be increased to between 20,000 and 50,000 copies per cell. This makes such constructs, and the vectors encoding such constructs, excellent for use in decoy, therapeutic editing and antisense protocols as well as for ribozyme formation. In addition, the molecules can be used as agonist or antagonist RNAs (affinity RNAs). Generally, applicant believes that the intramolecular base-paired interaction between the 5' terminus and the 3' region of the RNA should be in a double-stranded structure in order to achieve enhanced RNA accumulation.

Thus, in one preferred embodiment the invention features a pol. III promoter system (, a type 2 system) used to synthesize a chimeric RNA molecule which includes tRNA sequences and a desired RNA (e, a tRNA-based molecule).

The following exemplifies this invention with a type 2 pol III promoter and a tRNA gene. Specifically to illustrate the broad invention, the RNA molecule in the following example has an A box and a B box of the type 2 pol III promoter system and has a 5' terminus or region able to base-pair with at least 8 bases of a complementary 3' end or region of the same RNA molecule. This is meant to be a specific example. Those in the art will recognize that this is but one example, and other embodiments can be readily generated using other pol III promoter systems and techniques generally known in the art.

By "terminus" is meant the terminal bases of an RNA molecule, ending in a 3' hydroxyl or 5' phosphate or 5' cap moiety. By "region" is meant a stretch of bases 5' or 3' from the terminus that are involved in base-paired interactions. It need not be adjacent to the end of the RNA. Applicant has determined that base pairing of at least one end of the RNA molecule with a region not more than about 50 bases, and preferably only 20 bases, from the other end of the molecule provides a useful molecule able to be expressed at high levels.

By "3' region" is meant a stretch of bases 3' from the terminus that are involved in intramolecular base-paired interaction with complementary nucleotides in the 5' terminus of the same molecule. The 3' region can be designed to include the 3' terminus. The 3' region therefore is >0 nucleotides from the 3' terminus. For example, in the S35 construct described in the present invention (FIG. 7) the 3' region is one nucleotide from the 3' terminus. In another example, the 3' region is ~43 nt from 3' terminus. These examples are not meant to be limiting. Those in the art will recognize that other embodiments can be readily generated using techniques generally known in the art. Generally, it is preferred to have the 3' region within 100 bases of the 3' terminus.

By "tRNA molecule" is meant a type 2 pol III driven RNA molecule that is generally derived from any recognized tRNA gene. Those in the art will X recognize that DNA encoding such molecules is readily available and can be modified as desired to alter one or more bases within the DNA encoding the RNA molecule and/or the promoter system. Generally, but not always, such molecules include an A box and a B box that consist of sequences which are well known in the art (and examples of which can be found throughout the literature). These A and B boxes have a certain consensus sequence which is essential for a optimal pol III transcription.

By "chimeric tRNA molecule" is meant a RNA molecule that includes a pol III promoter (type 2) region. A chimeric tRNA molecule, for example, might contain an intramolecular base-paired structure between the 3' region and complementary 5' terminus of the molecule, and includes a foreign RNA sequence at any location within the molecule which does not affect the activity of the type 2 pol III promoter boxes. Thus, such a foreign RNA may be provided at the 3' end of the B box, or may be provided in between the A and the B box, with the B box moved to an appropriate location either within the foreign RNA or another location such that it is effective to provide pol III transcription. In one example, the RNA molecule may include a hammerhead ribozyme with the B box of a type 2 pol III promoter provided in stem II of the ribozyme. In a second example, the B box may be provided in stem IV region of a hairpin ribozyme. A specific example of such RNA molecules is provided below. Those in the art will recognize that this is but one example, and other embodiments can be readily generated using techniques generally known in the art By "desired RNA" molecule is meant any foreign RNA molecule which is useful from a therapeutic, diagnostic, or other viewpoint. Such molecules include antisense RNA molecules, decoy RNA molecules, enzymatic RNA, therapeutic editing RNA (Woolf and Stinchcomb, "Oligomer directed In situ reversion (ISR) of genetic mutations", filed Jul. 6, 1994, U.S. Ser. No. 08/271,280, hereby incorporated by reference) and agonist and antagonist RNA.

By "antisense RNA" is meant a non-enzymatic RNA molecule that binds to another RNA (target RNA) by means of RNA-RNA interactions and alters the activity of the target RNA (Eguchi et al., 1991 Annu. Rev. Biochem. 60, 631–652). By "enzymatic RNA" is meant an RNA molecule with enzymatic activity (Cech, 1988 *J. American. Med. Assoc.* 260, 3030–3035). Enzymatic nucleic acids (ribozymes) act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through base-pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990 Cell 63, 601–608). This is meant to be a specific example. Those in the art will recognize that this is but one example, and other embodiments can be readily generated using techniques generally known in the art.

By "therapeutic editing RNA" is meant an antisense RNA that can bind to its cellular target (RNA or DNA) and mediate the modification of a specific base (Woolf and Stinchcomb, supra).

By "agonist RNA" is meant an RNA molecule that can bind to protein receptors with high affinity and cause the stimulation of specific cellular pathways.

By "antagonist RNA" is meant an RNA molecule that can bind to cellular proteins and prevent it from performing its normal biological function (for example, see Tsai et al., 1992 *Proc. Natl. Acad. Sci.* USA 89, 8864–8868).

By "complementary" is meant a RNA sequence that can form hydrogen bond(s) with other RNA sequence by either traditional Watson-Crick or other non-traditional types (for example, Hoogsteen type) of base-pairing interaction.

In other aspects, the invention includes vectors encoding RNA molecules as described above, cells including such vectors, methods for producing the desired RNA, and use of the vectors and cells to produce this RNA.

By "vectors" is meant any nucleic acid- and/or viral-based technique used to deliver a desired nucleic acid.

Thus, the invention features a transcribed non-naturally occuring RNA molecule which includes a desired therapeutic RNA portion and an intramolecular stem formed by base-pairing interactions between a 3' region and complementary nucleotides at the 5' terminus in the RNA. The stem preferably includes at least 8 base pairs, but may have more, for example, 15 or 16 base pairs.

In preferred embodiments, the 5' terminus of the chimeric tRNA includes a portion of the precursor molecule of the primary tRNA molecule, of which ≧8 nucleotides are involved in base-pairing interaction with the 3' region; the chimeric tRNA contains A and B boxes; natural sequences 3' of the B box are deleted, which prevents endogenous RNA processing; the desired RNA molecule is at the 3' end of the B box; the desired RNA molecule is between the A and the B box; the desired RNA molecule includes the B box; the desired-RNA molecule is selected from the group consisting of antisense RNA, decoy RNA, therapeutic editing RNA, enzymatic RNA, agonist RNA and antagonist RNA; the molecule has an intramolecular stem resulting from a base-paired interaction between the 5' terminus of the RNA and a complementary 3' region within the same RNA, and includes at least 8 bases; and the 5' terminus is able to base pair with at least 15 bases of the 3' region.

In most preferred embodiments, the molecule is transcribed by a RNA polymerase III based promoter system, e.g., a type 2 pol III promoter system; the molecule is a chimeric tRNA, and may have the A and B boxes of a type 2 pol III promoter separated by between 0 and 300 bases; DNA vector encoding the RNA molecule of claim 1.

In other related aspects, the invention features an RNA or DNA vector encoding the above RNA molecule, with the portions of the vector encoding the RNA functioning as a RNA pol III promoter; or a cell containing the vector; co or a method to provide a desired RNA molecule in a cell, by introducing the molecule into a cell with an RNA molecule as described above. The cells can be derived from animals, plants or human beings.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1. Schematic representation of RNA polymerse III promoter structure. Arrow indicates the transcription start site and the direction of coding region. A, B and C, refer to consensus A, B and C box promoter sequences. I, refers to intermediate cis-acting promoter sequence. PSE, refers to proximal sequence element. DSE, refers to distal sequence element. ATF, refers to activating transcription factor binding element. ?, refers to cis-acting sequence element that has not been fully characterized. EBER, Epstein-Barr-virus-encoded-RNA. TATA is a box well known in the art.

FIG. 2. Sequence of the primary $tRNA_i^{met}$ and Δ3-5 transcripts. The A and B box are internal promoter regions necessary for pol III transcription. Arrows indicate the sites of endogenous tRNA processing. The Δ3-5 transcript is a truncated version of tRNA wherein the sequence 3' of B box has been deleted (Adeniyi-Jones et al., 1984 supra). This modification renders the Δ3-5 RNA resistant to endogenous tRNA processing.

FIG. 3. Schematic representation of RNA structural motifs inserted into the Δ3-5 RNA. Δ3-5/HHI- a hammerhead (HHI) ribozyme was cloned at the 3' region of Δ3-5 RNA; S3- a stable stem-loop structure was incorporated at the 3' end of the Δ3-5/HHI chimera; S5- stable stem-loop structures were incorporated at the 5' and the 3' ends of &3-5/HHI ribozyme chimera; S35-sequence at the 3' end of the Δ3-5/HHI ribozyme chimera was altered to enable duplex formation between the 5' end and a complementary 3' region of the same RNA; S35Plus- in addition to structural alterations of S35, sequences were altered to facilitate additional duplex formation within the non-ribozyme sequence of the Δ3-5/HHI chimera.

FIG. 4. Northern analysis to quantitate ribozyme expression in T cell lines transduced with Δ3-5 vectors. A) Δ3-5/HHI and its variants were cloned individually into the DC retroviral vector (Sullenger et al., 1990 supra). Northern analysis of ribozyme chimeras expressed In MT-2 cells was performed. Total RNA was isolated from cells (Chomczynski & Sacchi, 1987 *Analytical Biochemistry* 162, 156–159), and transduced with various constructs described in FIG. 3. Northern analysis was carried out using standard protocols (*Curr. Protocols Mol. Biol.* 1992, ed. Ausubel et al., Wiley & Sons, NY). Nomenclature is same as in FIG. 3.

This assay measures the level of expression from the type 2 pol III promoter. B) Expression of S35 constructs in MT2 cells. S35 (+ribozyme), S35 construct containing HHI ribozyme. S35 (−ribozyme), S35 construct containing no ribozyme.

FIG. 5. Ribozyme activity in total RNA extracted from transduced MT-2 cells. Total RNA was isolated from cells transduced with Δ3-5 constructs described in FIG. 4. In a standard ribozyme cleavage reaction, 5 μg total RNA and trace amounts of 5' terminus-labeled ribozyme target RNA were denatured separately by heating to 90° C. for 2 min in the presence of 50 mM Tris-HCl, pH 7.5 and 10 mM $MgCl_2$. RNAs were renatured by cooling the reaction mixture to 37° C. for 10–15 min. Cleavage reaction was initiated by mixing the labeled substrate RNA and total cellular RNA at 37° C. The reaction was allowed to proceed for −18 h, following which the samples were resolved on a 20% urea polyacrylamide gel. Bands were visualized by autoradiography.

FIG. 6. Ribozyme expression and activity levels in S35-transduced clonal CEM cell lines. A) Northern analysis of S35-transduced clonal CEM cell lines. Standard curve was generated by spiking known concentrations of in vitro transcribed S5 RNA into total cellular RNA isolated from non-transduced CEM cells. Pool, contains RNA from pooled cells transduced with S35 construct. Pool (−G418 for 3 Mo), contains RNA from pooled cells that were initially selected for resistance to G418 and then grown in the absence of G418 for 3 months. Lanes A through N contain RNA from individual clones that were generated from the pooled cells transduced with S35 construct. $tRNA_i^{met}$, refers to the endogenous tRNA. S35, refers to the position of the ribozyme band. M, marker lane. B) Activity levels in S35-transduced clonal CEM cell lines. RNA isolation and cleavage reactions were as described in FIG. 5. Nomenclature is same as in FIG. 6A except, S, 5' terminus-labeled substrate RNA. P, 8 nt 5' terminus-labeled ribozyme-mediated RNA cleavage product.

FIGS. 7 and 8 are proposed secondary structures of S35 and S35 containing a desired RNA (HHI), respectively. The position of HHI ribozyme is indicated in FIG. 8. Intramolecular stem refers to the stem structure formed due to an intramolecular base-paired interaction between the 3' sequence and the complementary 5' terminus. The length of the stem ranges from 15–16 base-pairs. Location of the A and the B boxes are shown.

FIGS. 9 and 10 are proposed secondary structures of S35 plus and S35 plus containing HHI ribozyme.

FIGS. 11 a,b and 12 a, b are the nucleotide base sequences of S35, HHIS35, S35 Plus, and HHIS35 Plus respectively.

FIG. 13 is a general formula for pol III RNA of this invention.

Figure 15:
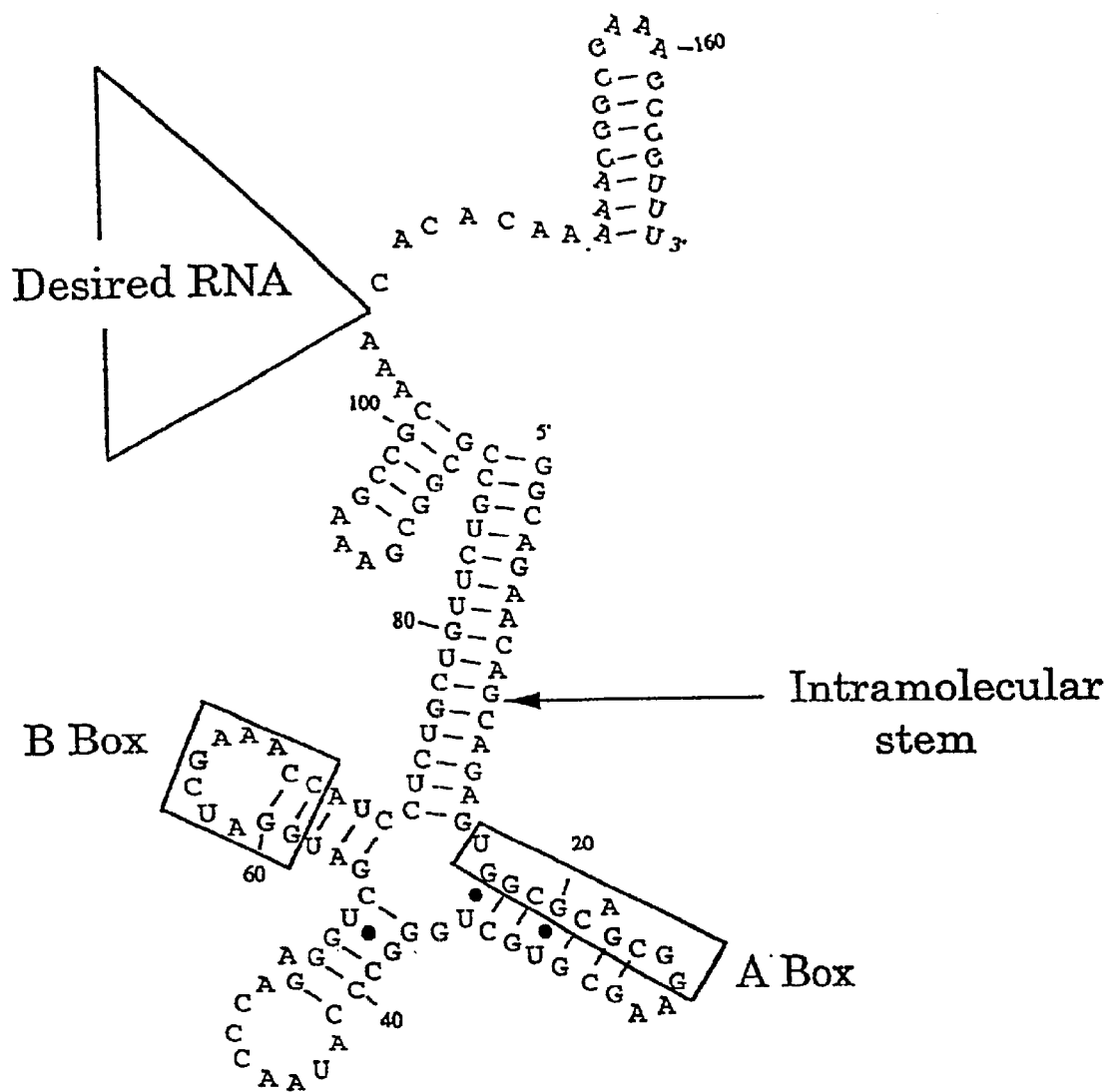
Figure 15:
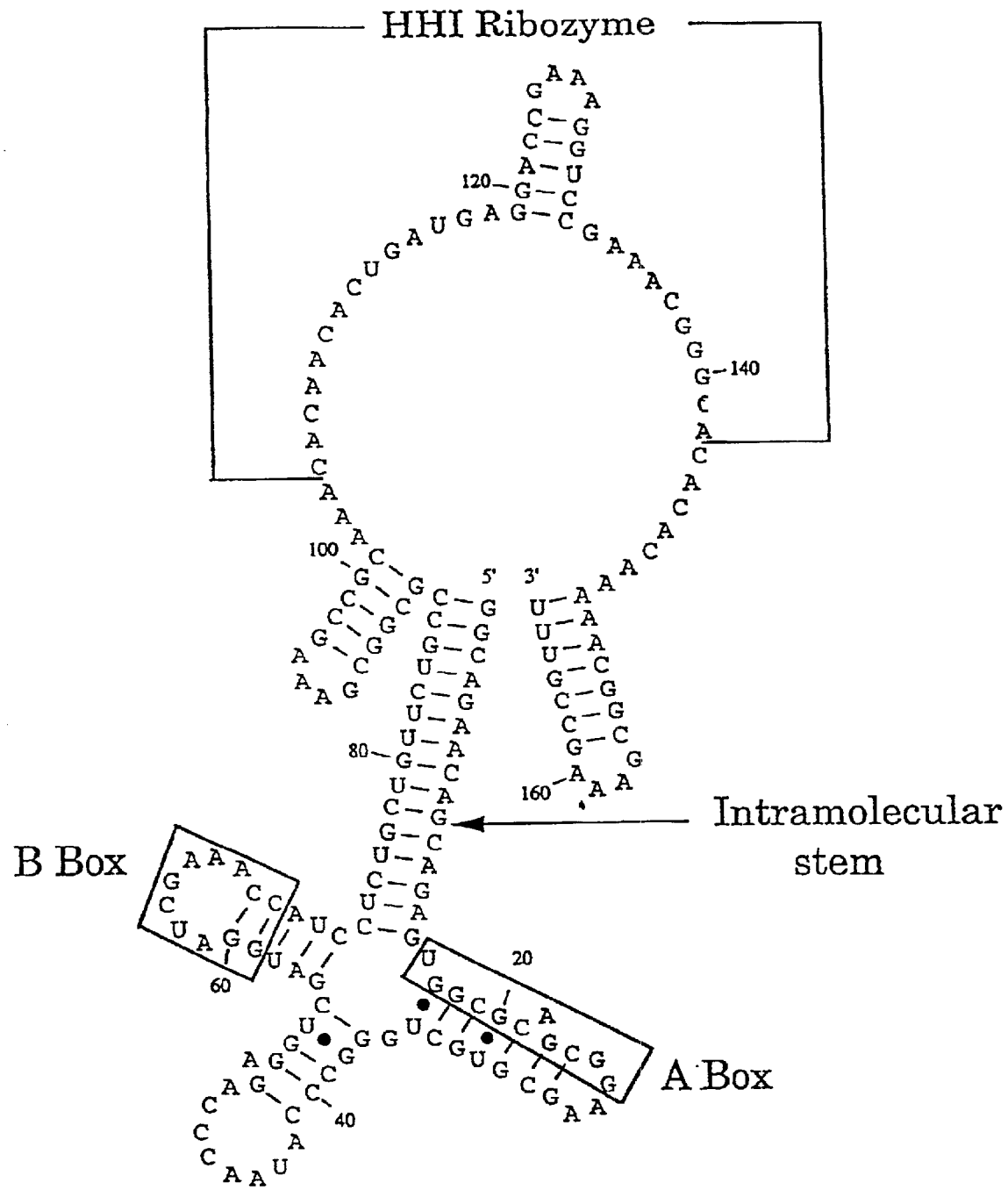

FIGS. 15A and B contain proposed secondary structures of 5T construct alone and 5T contruct containing a desired RNA (HHI ribozyme) respectively.

FIG. 16 is a diagrammatic representation of TRZ-tRNA chimeras. The site of desired RNA insertion is indicated.

Figure 17A:
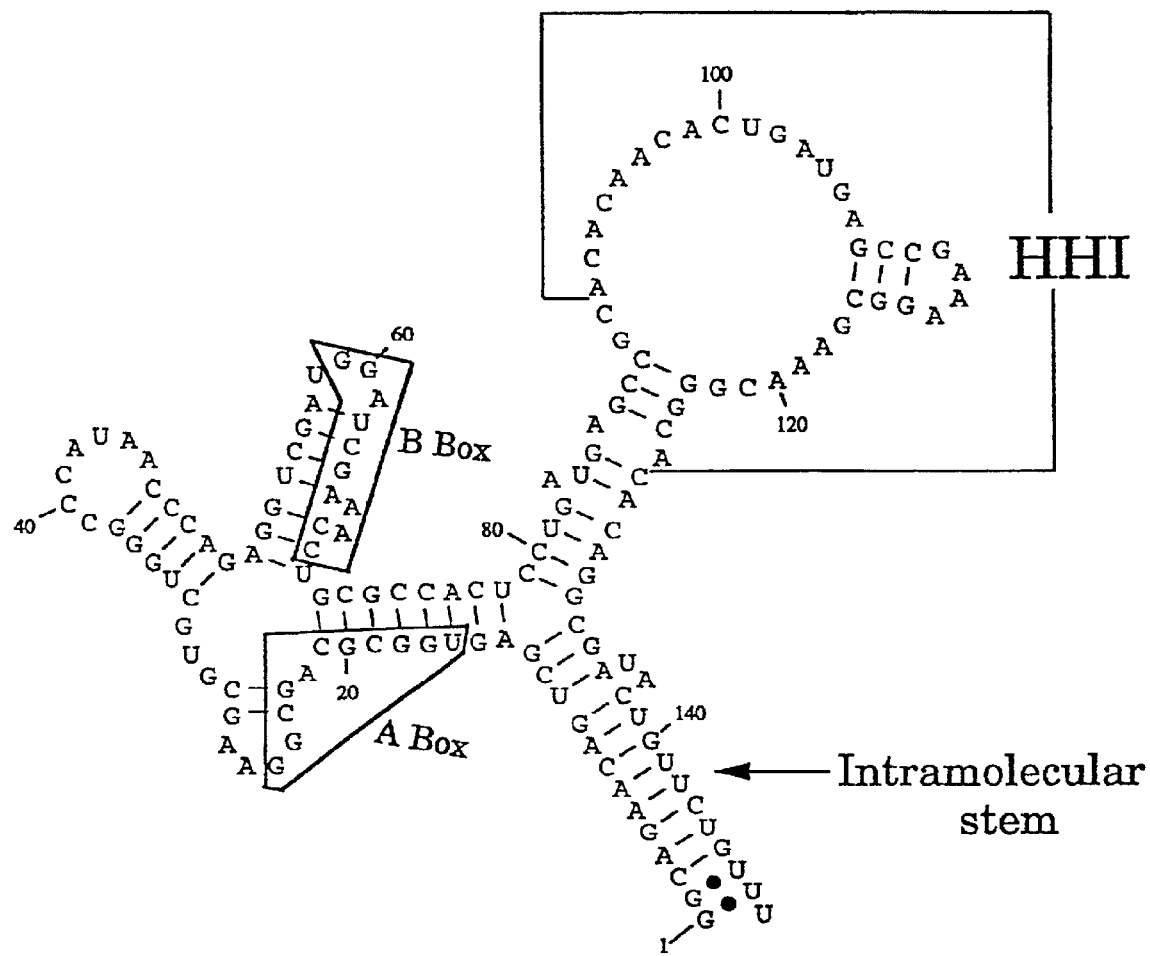

FIG. 17A shows the general structure of HHITRZ-A ribozyme chimera. A hammerhead ribozyme targeted to site I is inserted into the stem II region of TRZ-tRNA chimera. B shows the general structure of HPITRZ-A ribozyme chimera. A hairpin ribozyme targeted to site I is cloned into the indicated region of TRZ-tRNA chimera.

Figure 18:
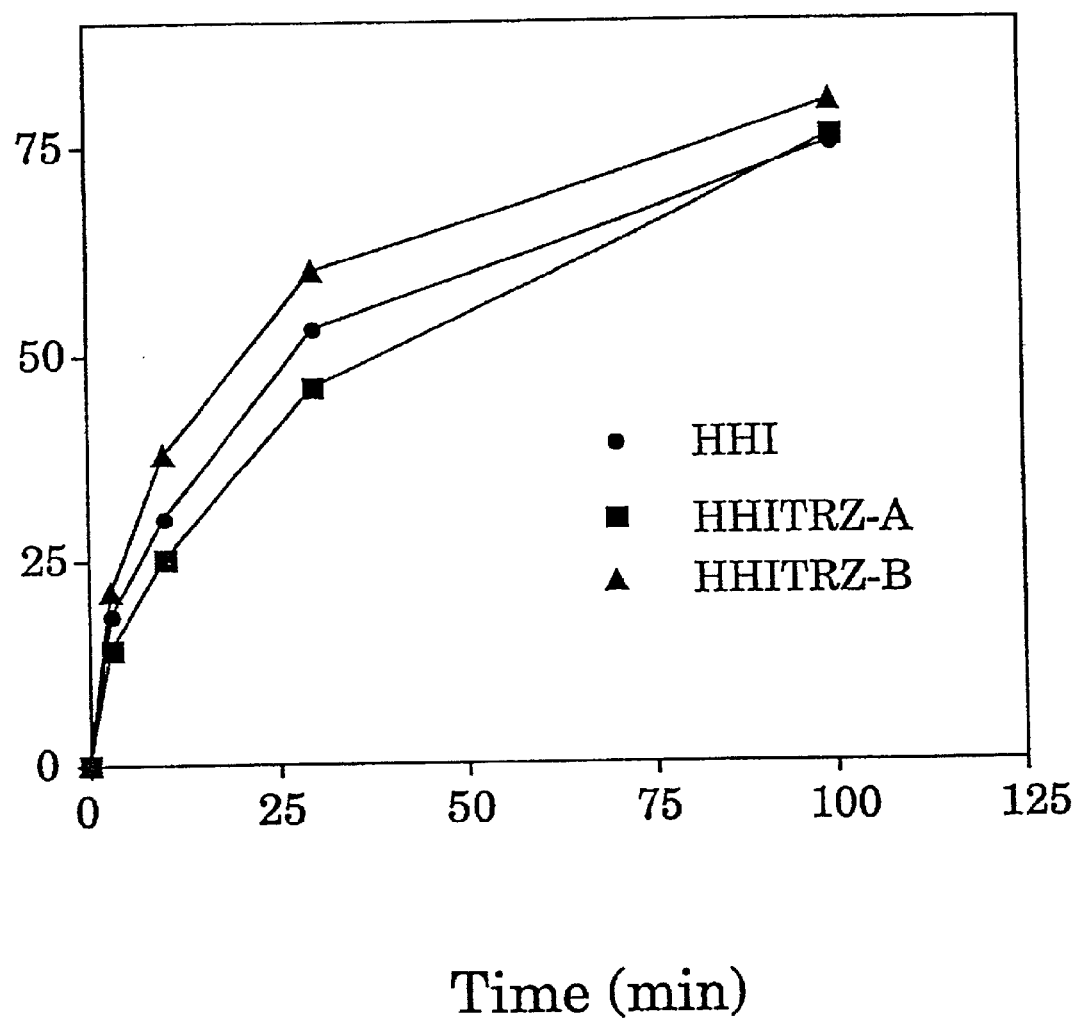

FIG. 18 shows a comparison of RNA cleavage activity of HHITRZ-A, HHITRZ-B and a chemically synthesized HHI hammerhead ribozymes.

FIG. 19 is a diagrammatic representation of a U6-S35 Chimera. The S35 motif and the site of insertion of a desired RNA are indicated. This chimeric RNA transcript is under the control of a U6 small nuclear RNA (snRNA) promoter.

FIG. 20 is a diagrammatic representation of a U6-S35-ribozyme chimera. The chimera contains a hammerhead ribozyme targeted to site I (HHI).

FIG. 21 is a diagrammatic representation of a U6-S35-ribozyme chimera. The chimera contains a hammerhead ribozyme targeted to site II (HHII).

FIG. 22 shows RNA cleavage reaction catalyzed by a synthetic hammerhead ribozyme (HHI) and by an in vitro transcript of U6-S35-HHI hammerhead ribozyme.

FIG. 23 shows stability of U6-S35-HHII RNA transcript in 293 mammalian cells as measured by actinomycin D assay.

FIG. 24 is a diagrammatic representation of an adenovirus VA1 RNA. Various domains within the RNA secondary structure are indicated.

FIG. 25A shows a secondary structure model of a VA1-S35 chimeric RNA containing the promoter elements A and B box. The site of insertion of a desired RNA and the S35 motif are indicated. The transcription unit also contains a stable stem (S35-like motif) in the central domain of the VA1 RNA which positions the desired RNA away from the main transcript as an independent domain. B shows a VA1-chimera which consists of the terminal 75 nt of a VA1 RNA followed by the HHI ribozyme.

FIG. 26 shows a comparison of stability of VA1-chimeric RNA vs VA1-S35-chimeric RNA as measured by actinomycin D assay. VA1-chimera consists of terminal 75 nt of VA1 RNA followed by HHI ribozyme. VA1-S35-chimera structure and sequence is shown in FIG. 25.

To make internally-labeled substrate RNA for trans-ribozyme cleavage reactions, a 613 nt region (containing site I) was synthesized by PCR using primers that place the T7 RNA promoter upstream of the amplified sequence. Target RNA was transcribed, using T7 RNA polymerase, in a standard transcription buffer in the presence of [α-$^{32}$P]CTP. The reaction mixture was treated with 15 units of ribonuclease-free DNaseI, extracted with phenol followed chloroform:isoamyl alcohol (25:1), precipitated with isopropanol and washed with 70% ethanol. The dried pellet was resuspended in 20 μl DEPC-treated water and stored at −20° C.

Unlabeled ribozyme (200 nM) and internally labeled 613 nt substrate RNA (<10 nM) were denatured and renatured separately in a standard cleavage buffer (containing 50 mM Tris.HCl pH 7.5 and 10 mM $MgCl_2$) by heating to 90° C. for 2 min. and slow cooling to 37° C. for 10 min. The reaction was initiated by mixing the ribozyme and substrate mixtures and incubating at 37° C. Aliquots of 5 μl were taken at regular time intervals, quenched by adding an equal volume of 2×formamide gel loading buffer and frozen on dry ice. The samples were resolved on 5% polyacrylamide sequencing gel and results were quantitatively analyzed by radio-analytic imaging of gels with a Phosphorlmager (Molecular Dynamics, Sunnyvale, Calif.).

RNA Therapy

Few antiviral drug therapies are available that effectively inhibit established viral infections. Consequently, prophylactic immunization has become the method of choice for protection against viral pathogens. However, effective vaccines for divergent viruses such as those causing the common cold, and HIV, the etiologic agent of AIDS, may not be feasible. Consequently, new antiviral strategies are being developed for combating viral infections.

Gene therapy represents a potential alternative strategy, where antiviral genes are stably transferred into susceptible cells. Such gene therapy approaches have been termed "intracellular immunization" since cells expressing antiviral genes become immune to viral infection (Baltimore, 1988 *Nature* 335, 395–396). Numerous forms of antiviral genes have been developed, including protein-based antivirals such as transdominant inhibitory proteins (Malim et al., 1993*J. Exp. Med.*, Bevec et al., 1992 *P.N.A.S.* (USA) 89, 9870–9874; Bahner et al., 1993 *J. Virol.* 67, 3199–3207) and viral-activated suicide genes (Ashorn et al., 1990 *P.N.A.S.* (USA) 87, 8889–8893). Although effective in tissue culture, protein-based antivirals have the potential to be immunogenic in vivo. It is therefore conceivable that treated cells expressing such foreign antiviral proteins will be eradicated by normal immune functions. Alternatives to protein based antivirals are RNA based molecules such as antisense RNAs, decoy RNAs, agonist RNAs, antagonist RNAs, therapeutic editing RNAs and ribozymes. RNA is not immunogenic; therefore, cells expressing such therapeutic RNAs are not susceptible to immune eradication.

In order for RNA-based gene therapy approaches to be effective, sufficient amounts of the therapeutic RNA must accumulate in the appropriate intracellular compartment of the treated cells. Accumulation is a function of both promoter strength of the antiviral gene, and the intracellular stability of the antiviral RNA. Both RNA polymerase II (pol II) and RNA polymerase III (pol III) based expression systems have been used to produce therapeutic RNAs in cells (Sarver & Rossi, 1993 *AIDS Res. & Human Retroviruses* 9, 483–487; Yu et al., 1993 *P.N.A.S.*(USA) 90, 6340–6344). However, pol III based expression cassettes are theoretically more attractive for use in expressing antiviral RNAs for the following reasons. Pol II produces messenger RNAs located exclusively in the cytoplasm, whereas pol III produces functional RNAs found in both the nucleus and the cytoplasm. Pol II promoters tend to be more tissue restricted, whereas pol III genes encode tRNAs and other functional RNAs necessary for basic "housekeeping" functions in all cell types. Therefore, pol III promoters are likely to be expressed in all tissue types. Finally, pol III transcripts from a given gene accumulate to much greater levels in cells relative to pol II genes.

Intracellular accumulation of therapeutic RNAs is also dependent on the method of gene transfer used. For example, the retroviral vectors presently used to accomplish stable gene transfer, integrate randomly into the genome of target cells. This random integration leads to varied expression of the transferred gene in individual cells comprising the bulk treated cell population. Therefore, for maximum effectiveness, the transferred gene must have the capacity to express therapeutic amounts of the antiviral RNA in the entire treated cell population, regardless of the integration site.

Pol III System

The following is just one non-limiting example of the invention. A pol III based genetic element derived from a human $tRNA_i^{met}$ gene and termed Δ3-5 (FIG. 2; Adeniyi-Jones et al., 1984 supra), has been adapted to express antiviral RNAs (Sullenger et al., 1990 *Mol. Cell. Biol.* 10, 6512–6523). This element was inserted into the DC retroviral vector (Sullenger et al., 1990 *Mol. Cell., Biol.* 10, 6512–6523) to accomplish stable gene transfer, and used to express antisense RNAs against moloney murine leukemia virus and anti-HIV decoy RNAs (Sullenger et al., 1990 *Mol. Cell. Biol.* 10, 6512–6523; Sullenger et al., 1990 *Cell* 63, 601–608; Sullenger et al., 1991 *J. Virol.* 65, 6811–6816; Lee et al., 1992 *The New Biologist* 4, 66–74). Clonal lines are expanded from individual cells present in the bulk population, and therefore express similar amounts of the therapeutic RNA in all cells. Development of a vector system that generates therapeutic levels of therapeutic RNA in all treated cells would represent a significant advancement in RNA based gene therapy modalities.

Figure 3:
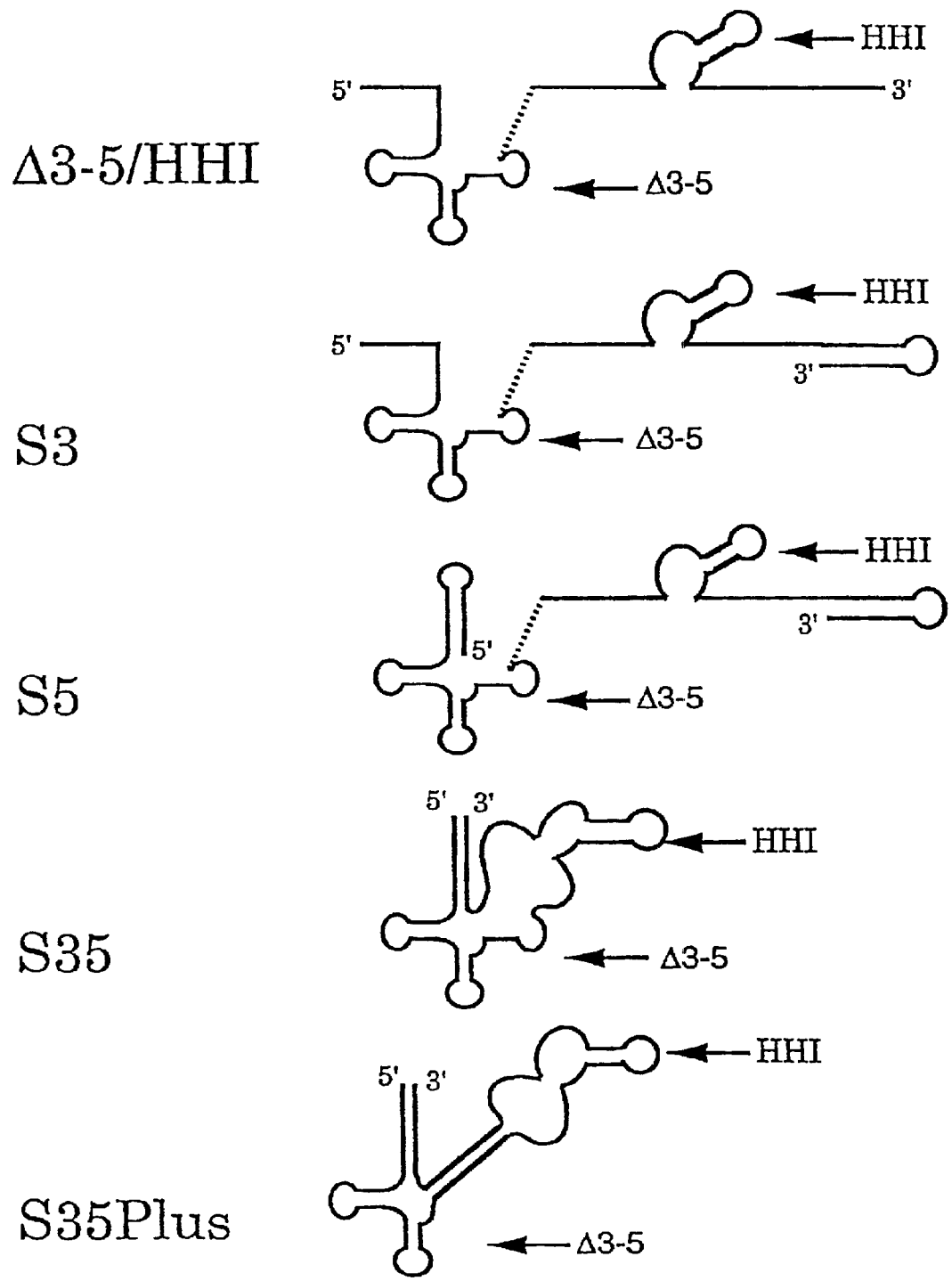

Applicant examined hammerhead (HHI) ribozyme (RNA with enzymatic activity) expression in human T cell lines using the Δ3-5 vector system (These constructs are termed "Δ3-5/HHI"; FIG. 3). On average, ribozymes were found to accumulate to less than 100 copies per cell in the bulk T cell populations. In an attempt to improve expression levels of the Δ3-5 chimera, the applicant made a series of modified Δ3-5 gene units containing enhanced promoter elements to increase transcription rates, and inserted structural elements to improve the intracellular stability of the ribozyme transcripts (FIG. 3). One of these modified gene units, termed S35, gave rise to more than a 100-fold increase in ribozyme accumulation in bulk T cell populations relative to the original Δ3-5/HHI vector system. Ribozyme accumulation in individual clonal lines from the pooled T cell populations ranged from 10 to greater than 100 fold more than those achieved with the original Δ3-5/HHI version of this vector.

The S35 gene unit may be used to express other therapeutic RNAs including, but not limited to, ribozymes, antisense, decoy, therapeutic editing, agonist and antagonist RNAs. Application of the S35 gene unit would not be limited to antiviral therapies, but also to other diseases, such as cancer, in which therapeutic RNAs may be effective. The S35 gene unit may be used in the context of other vector systems besides retroviral vectors, including but not limited to, other stable gene transfer systems such as adeno-associated virus (AAV; Carter, 1992 *Curr. Opin. Genet. Dev.* 3, 74), as well as transient vector systems such as plasmid delivery and adenoviral vectors (Berkner, 1988 *BioTechniques* 6, 616–629).

As described below, the S35 vector encodes a truncated version of a tRNA wherein the 3' region of the RNA is base-paired to complementary nucleotides at the 5' terminus, which includes the 5' precursor portion that is normally processed off during tRNA maturation. Without being bound by any theory, Applicant believes this feature is important in the level of expression observed. Thus, those in the art can now design equivalent RNA molecules with such high expression levels. Below are provided examples of the methodology by which such vectors and tRNA molecules can be made.

Δ3-5 Vectors

Figure 2:
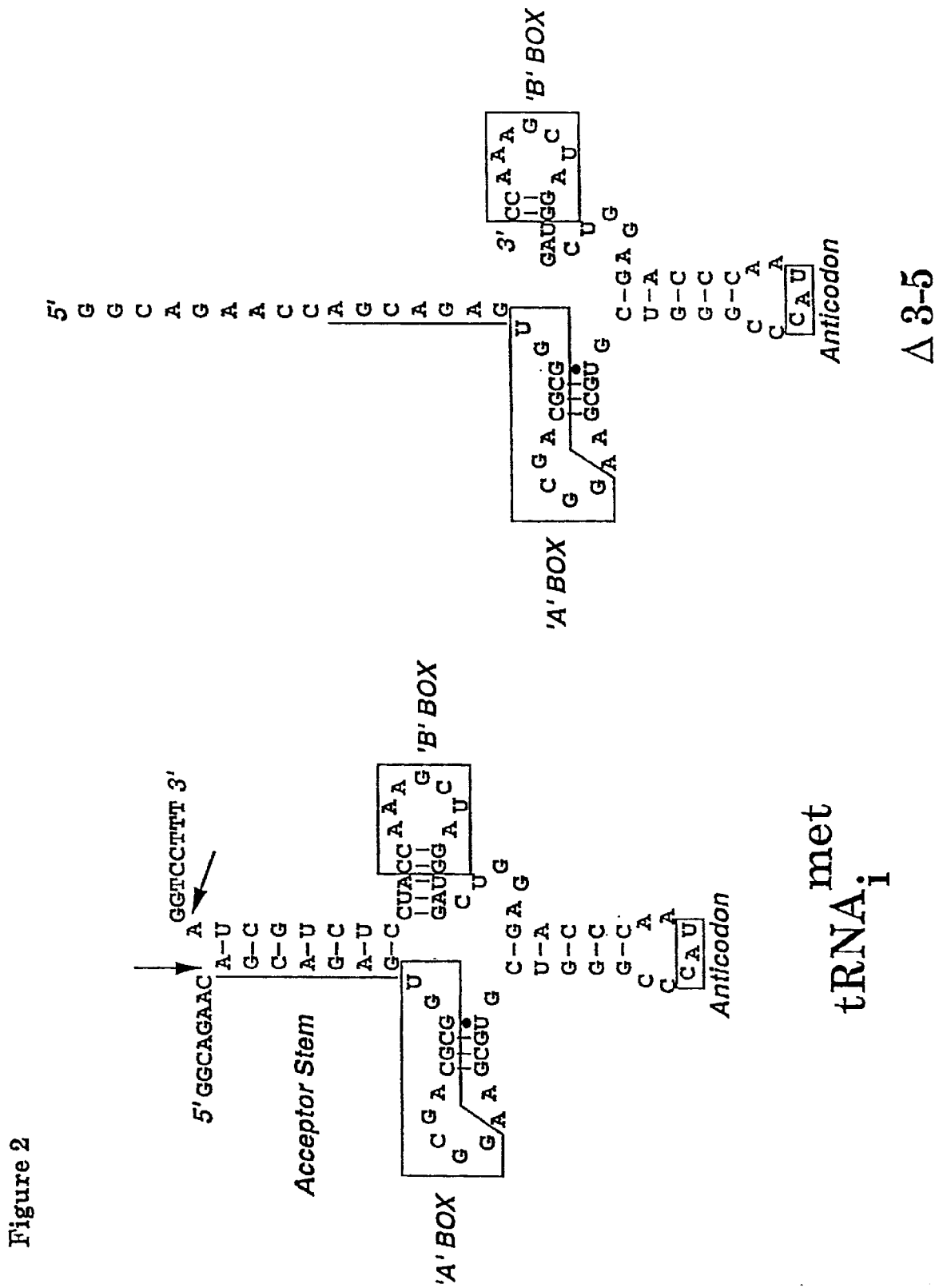

The use of a truncated human $tRNA_i^{met}$ gene, termed Δ3-5 (FIG. 2; Adeniyi-Jones et al., 1984 supra), to drive expression of antisense RNAs, and subsequently decoy RNAs (Sullenger et al., 1990 supra) has recently been reported. Because tRNA genes utilize internal pol III promoters, the antisense and decoy RNA sequences were expressed as chimeras containing $tRNA_i^{met}$ sequences. The truncated tRNA genes were placed into the U3 region of the 3' moloney murine leukemia virus vector LTR (Sullenger et al., 1990 supra).

Base-Paired Structures

Figure 4A:
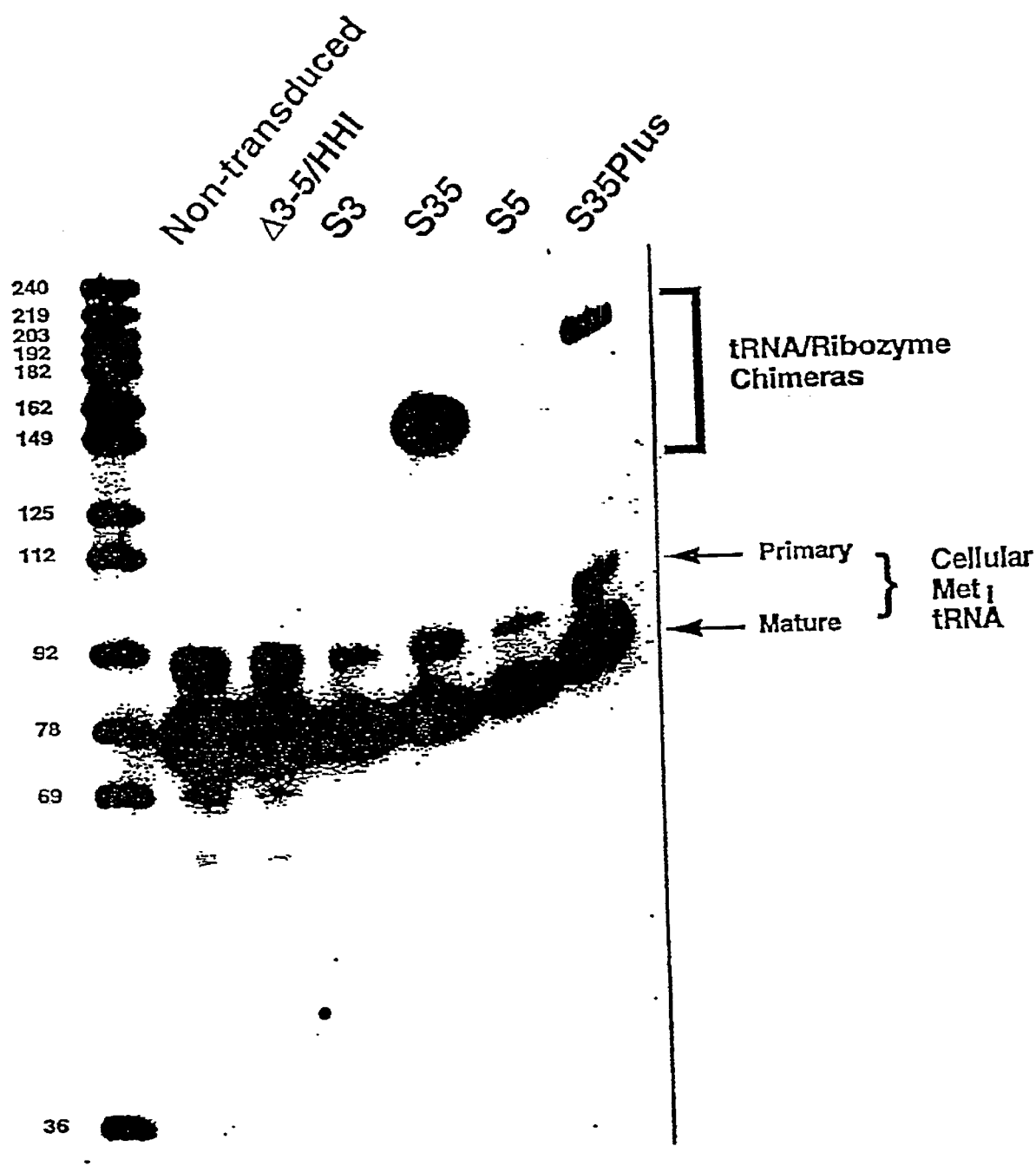

Since the Δ3-5 vector combination has been successfully used to express inhibitory levels of both antisense and decoy RNAs, applicant cloned ribozyme-encoding sequences (termed as "Δ3-5/HHI") into this vector to explore its utility for expressing therapeutic ribozymes. However, low ribozyme accumulation in human T cell lines stably transduced with this vector was observed (FIG. 4A). To try and improve accumulation of the ribozyme, S applicant incorporated various RNA structural elements (FIG. 3) into one of the ribozyme chimeras (Δ3-5/HHI).

Two strategies were used to try and protect the termini of the chimeric transcripts from exonucleolytic degredation. One strategy involved the incorporation of stem-loop structures into the termini of the transcript. Two such constructs were cloned, S3 which contains a stem-loop structure at the 3' end, and S5 which contains stem-loop structures at both ends of the transcript (FIG. 3). The second strategy involved modification of the 3' terminal sequences such that the 5' terminus and the 3' end sequences can form a stable base-paired stem. Two such constructs were made: S35 in which the 3' end was altered to hybridize to the 5' leader and acceptor stem of the $tRNA_i^{met}$ domain, and S35Plus which was identical to S35 but included more extensive structure formation within the non-ribozyme portion of the Δ3-5 chimeras (FIG. 3). These stem-loop structures are also intended to sequester non-ribozyme sequences in structures that will prevent them from interfering with the catalytic activity of the ribozyme. These constructs were cloned, producer cell lines were generated, and stably-transduced human MT2 (Harada et al., 1985 supra) and CEM (Nara & Fischinger, 1988 supra) cell lines were established (*Curr. Protocols Mol. Biol.* 1992, ed. Ausubel et al., Wiley & Sons, NY). The RNA sequences and structure of S35 and S35 Plus are provided in FIGS. 7–12.

Figure 14:
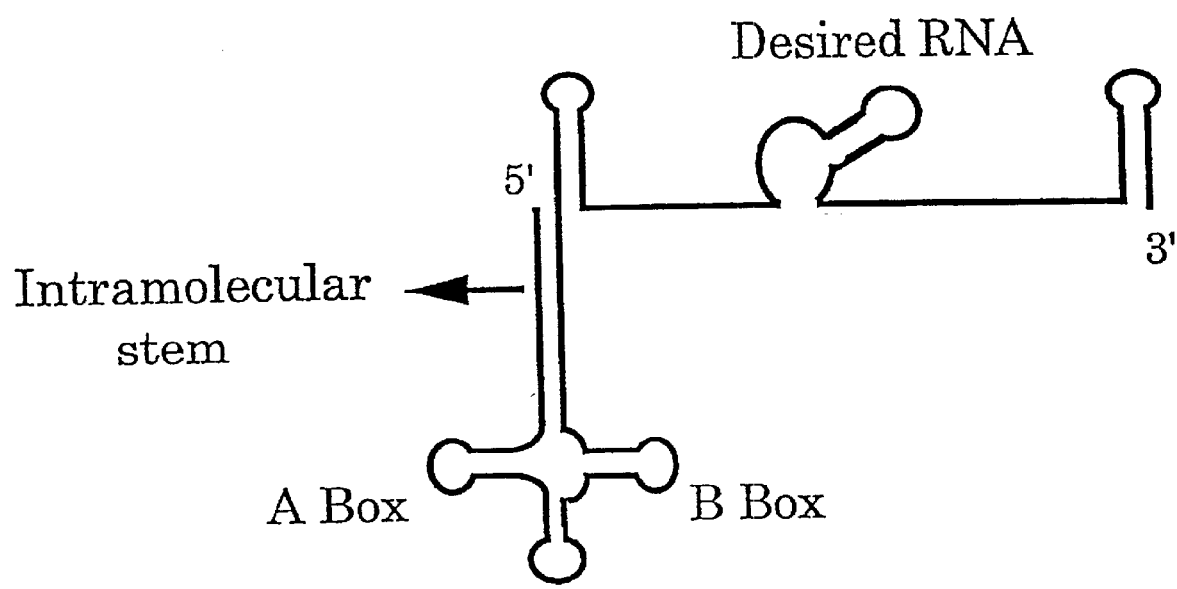
FIG. 14 is a digrammatic representation of 5T construct. In this construct the desired RNA is located 3' of the intramolecular stem.

Referring to FIG. 13, there is provided a general structure for a chimeric RNA molecule of this invention. Each N independently represents none or a number of bases which may or may not be base paired. The A and B boxes are optional and can be any known A or B box, or a consensus sequence as exemplified in the figure. The desired nucleic acid to be expressed can be any location in the molecule, but preferably is on those places shown adjacent to or between the A and B boxes (designated by arrows). FIG. 14 shows one example of such a structure in which a desired RNA is provided 3' of the intramolecular stem. A specific example of such a construct is provided in FIGS. 15a and 15b.

EXAMPLE 1

Cloning of Δ3-5-Ribozyme Chimera

Oligonucleotides encoding the S35 insert that overlap by at least 15 nucleotides were designed (5' GATCCACTCT-GCTGTTCTGTTTTTGA 3' (SEQ ID NO:21) and 5' CGCGTCAAAAACAGAACAGCAGAGTG 3'(SEQ ID NO:22). The oligonucleotides (10 μM each) were denatured by boiling for 5 min in a buffer containing 40 mM Tris.HCl, pH8.0. The oligonucleotides were allowed to anneal by snap cooling on ice for 10–15 min.

The annealed oligonucleotide mixture was converted into a double-stranded molecule using Sequenase® enzyme (US Biochemicals) in a buffer containing 40 mM Tris.HCl, pH7.5, 20 mM $MgCl_2$, 50 mM NaCl, 0.5 mM each of the four deoxyribonucleotide triphosphates, 10 mM DTT. The reaction was allowed to proceed at 37° C. for 30 min. The reaction was stopped by heating to 70° C. for 15 min.

The double stranded DNA was digested with appropriate restriction endonucleases (BamHI and MluI) to generate ends that were suitable for cloning into the Δ3-5 vector.

The double-stranded insert DNA was ligated to the Δ3-5 vector DNA by incubating at room temperature (about 20°

C.) for 60 min in a buffer containing 66 mM Tris.HCl, pH 7.6, 6.6 mM MgCl$_2$, 10 mM DTT, 0.066 ΔM ATP and 0.1U/µl T4 DNA Ligase (US Biochemicals).

Competent *E. coli* bacterial strain was transformed with the recombinant vector DNA by mixing the cells and DNA on ice for 60 min. The mixture was heat-shocked by heating to 37° C. for 1 min. The reaction mixture was diluted with LB media and the cells were allowed to recover for 60 min at 37° C. The cells were plated on LB agar plates and incubated at 37° C. for –18 h.

Plasmid DNA was isolated from an overnight culture of recombinant clones using standard protocols (Ausubel et al., *Curr. Protocols Mol. Biology* 1990, Wiley & Sons, NY).

The identity of the clones were determined by sequencing the plasmid DNA using the Sequenase® DNA sequencing kit (US Biochemicals).

The resulting recombinant Δ3-5 vector contains the S35 sequence. The HHI encoding DNA was cloned into this Δ3-5-S35 containing vector using SacII and BamHI restriction sites.

EXAMPLE 2

Northern Analysis

Figure 4:
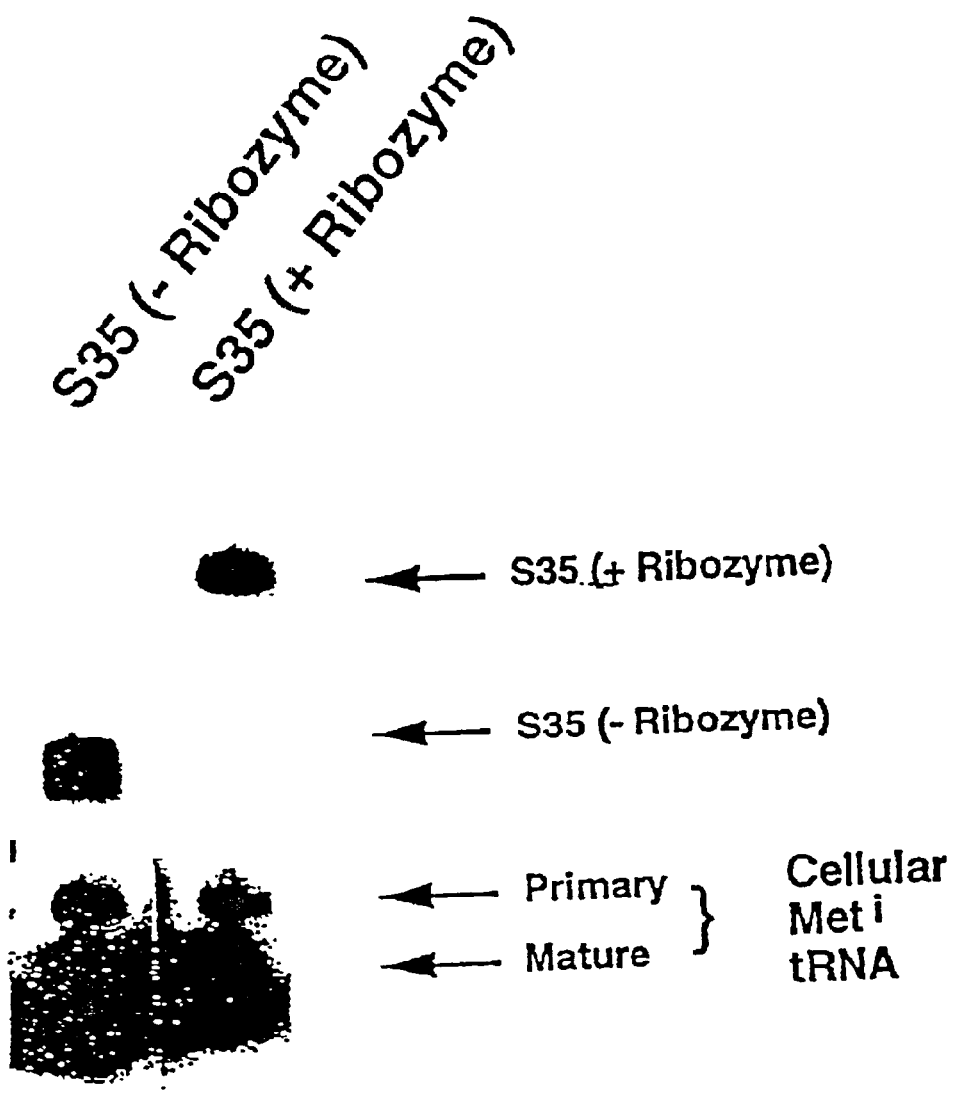

RNA from the transduced MT2 cells were extracted and the presence of Δ3-5/ribozyme chimeric transcripts were assayed by Northern analysis (*Curr. Protocols Mol. Biol.* 1992, ed. Ausubel et al., Wiley & Sons, NY). Northern analysis of RNA extracted from MT2 transductants showed that Δ3-5/ribozyme chimeras of appropriate sizes were expressed (FIG. 4). In addition, these results demonstrated the relative differences in accumulation among the different constructs (FIG. 4). The pattern of expression seen from the Δ3-5/HHI ribozyme chimera was similar to 12 other ribozymes cloned into the Δ3-vector (not shown). In MT-2 cell line, Δ3-5/HHI ribozyme chimeras accumulated, on average, to less than 100 copies per cell.

Addition of a stem-loop onto the 3' end of Δ3-5/HHI did not lead to increased Δ3-5 levels (S3 in FIG. 4). The S5 construct containing both 5' and 3' stem-loop structures also did not lead to increased ribozyme levels (FIG. 4).

Interestingly, the S35 construct expression in MT2 cells was about 100-fold more abundant relative to the original Δ3-5/HHI vector transcripts (FIG. 4). This may be due to increased stability of the S35 transcript.

EXAMPLE 3

Cleavage Activity

Figure 5:
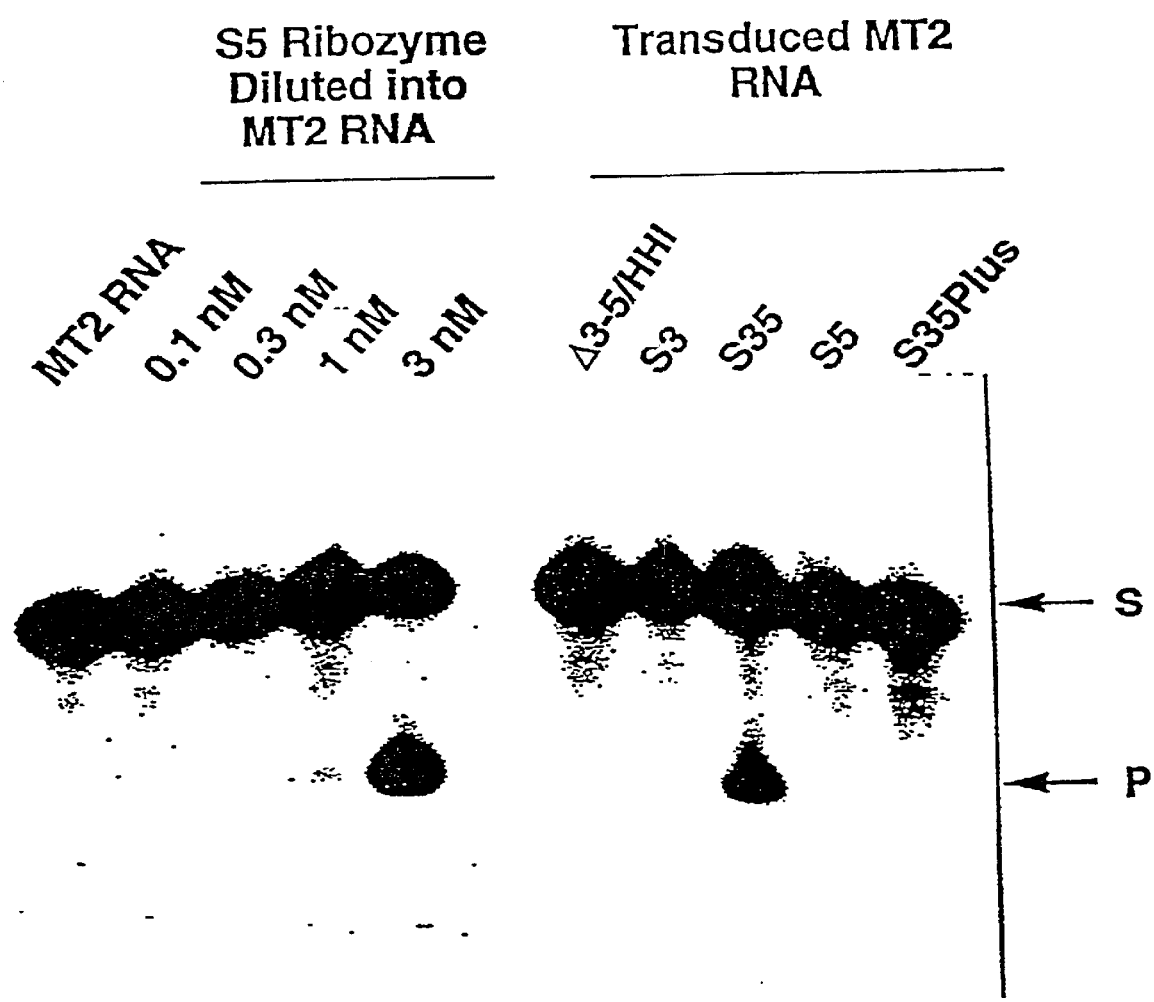

To assay whether ribozymes transcribed in the transduced cells contained cleavage activity, total RNA extracted from the transduced MT2 T cells were incubated with a labeled substrate containing the HHI cleavage site (FIG. 5). Ribozyme activity in all but the S35 constructs, was too low to detect. However, ribozyme activity was detectable in S35-transduced T cell RNA. Comparison of the activity observed in the S35-transduced MT2 RNA with that seen with MT2 RNA in which varying amounts of in vitro transcribed S5 ribozyme chimeras, indicated that between 1-3 nM of S35 ribozyme was present in S35-transduced MT2 RNA. This level of activity corresponds to an intracellular concentration of 5,000-15,000 ribozyme molecules per cell.

EXAMPLE 5

Clonal Variation

Figure 6A:
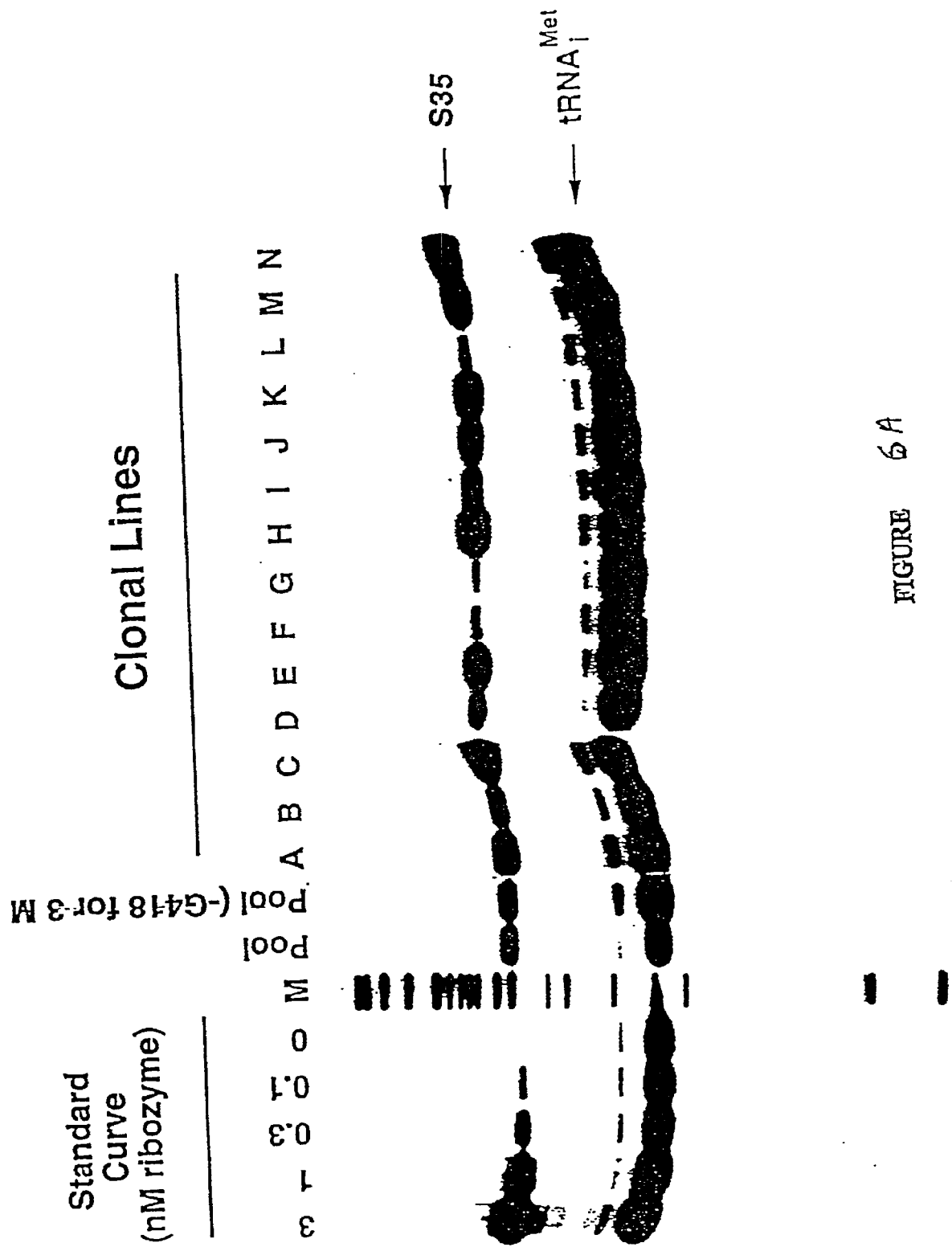
Figure 6B:
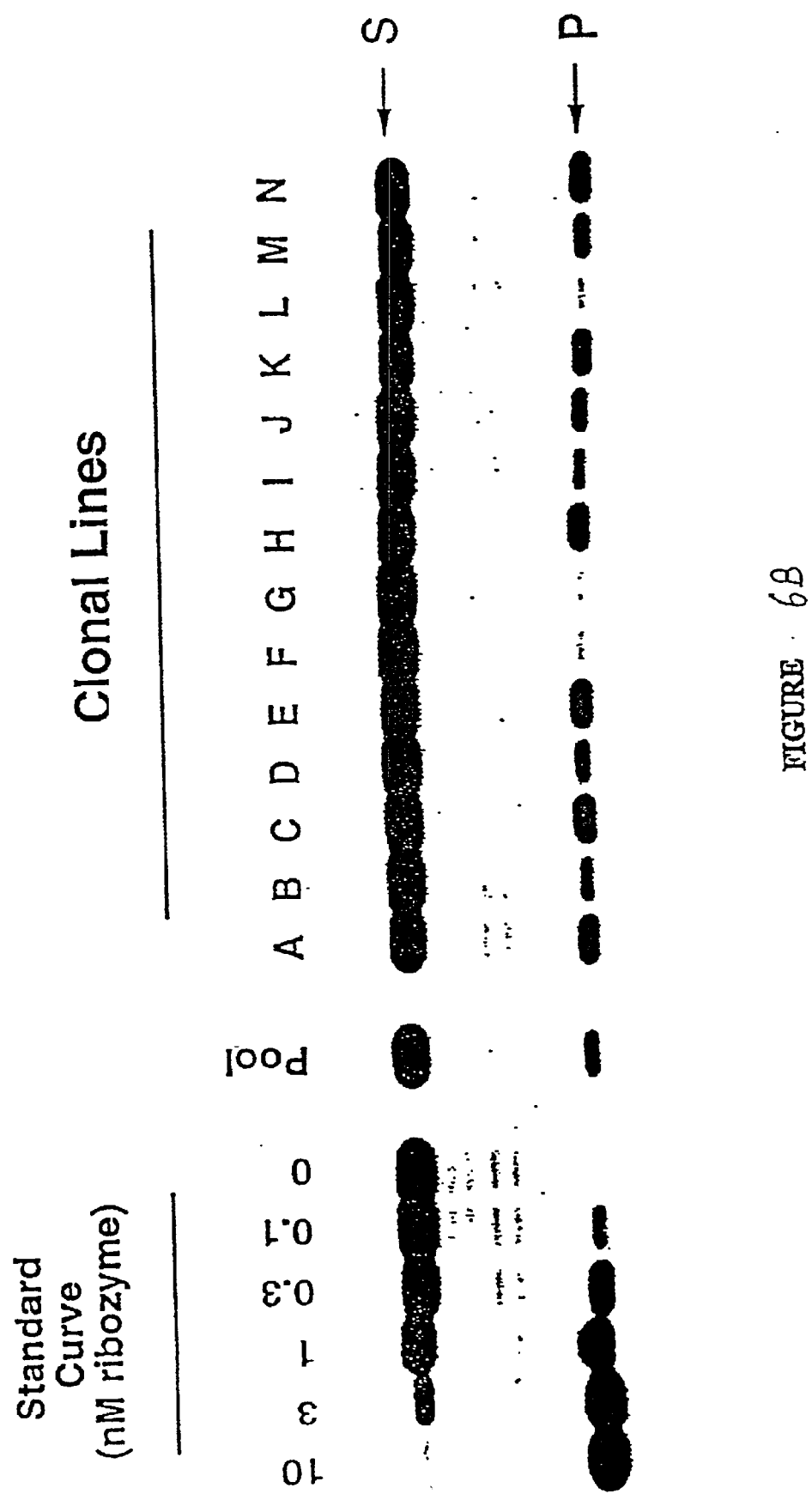
Figure 7:
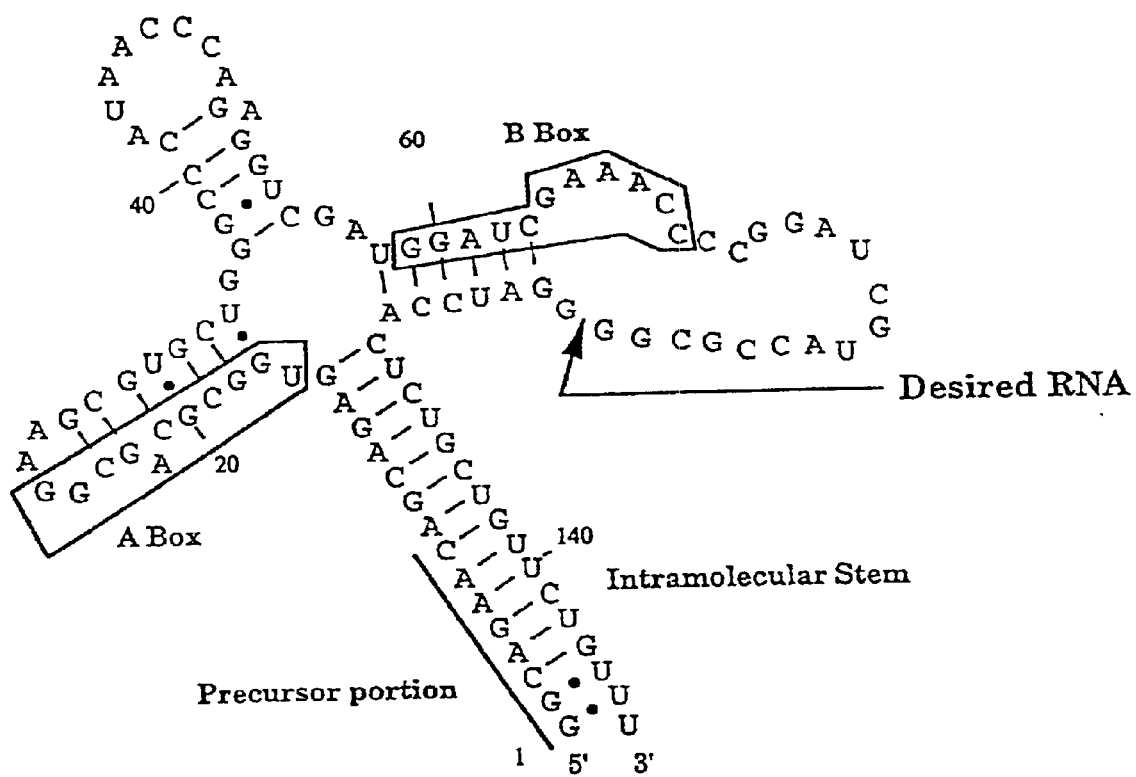
Figure 8:
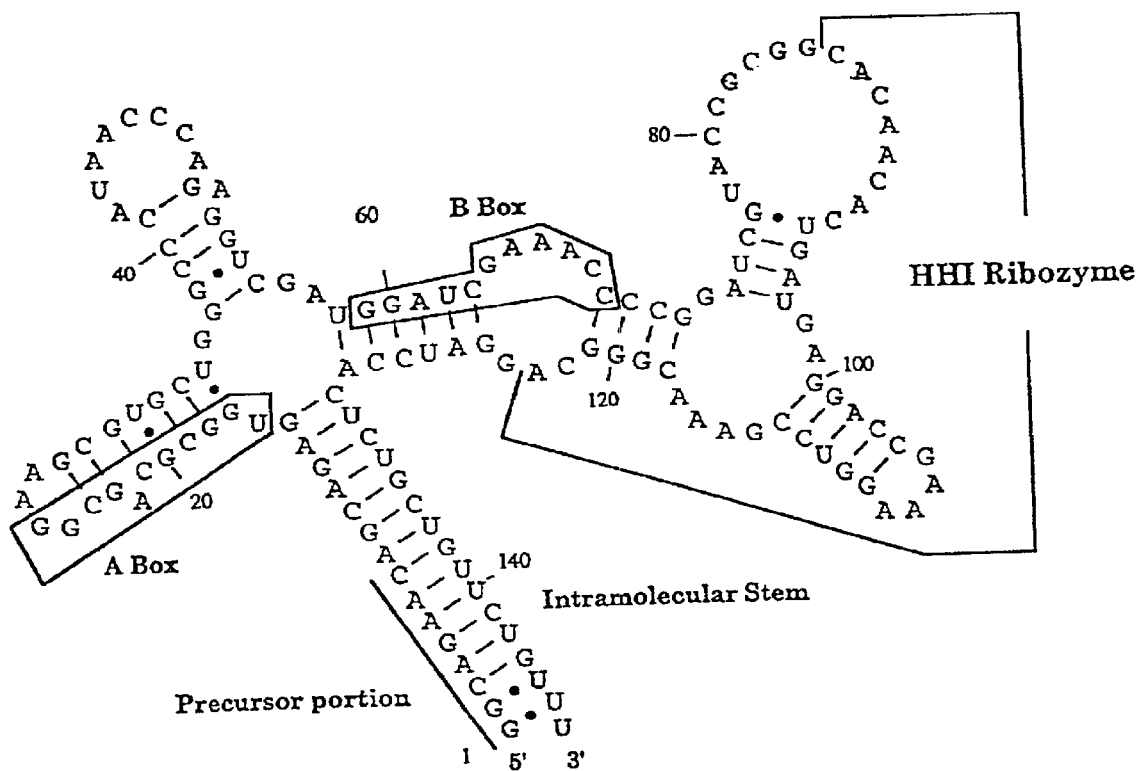
Figure 9:
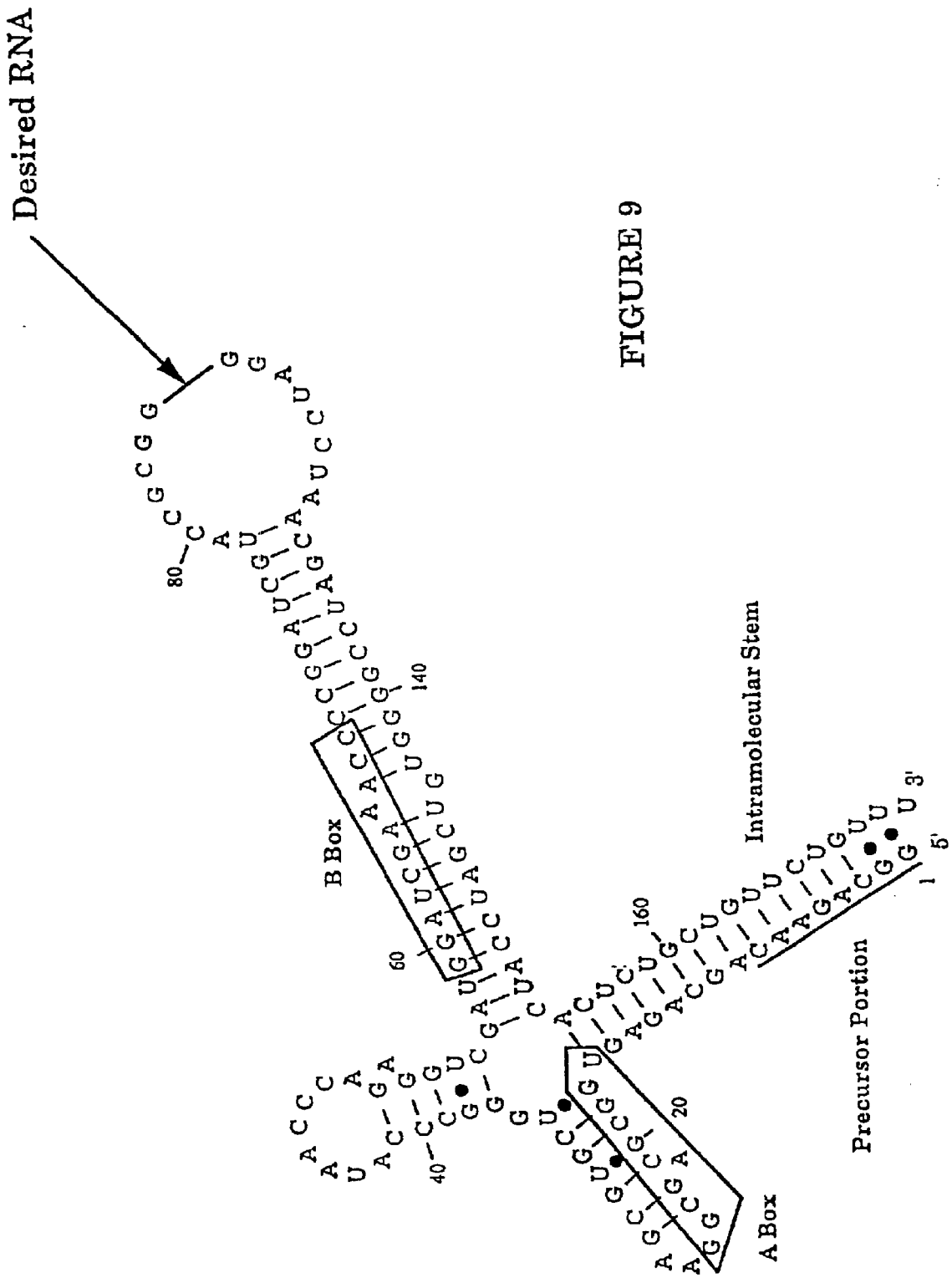
Figure 10:
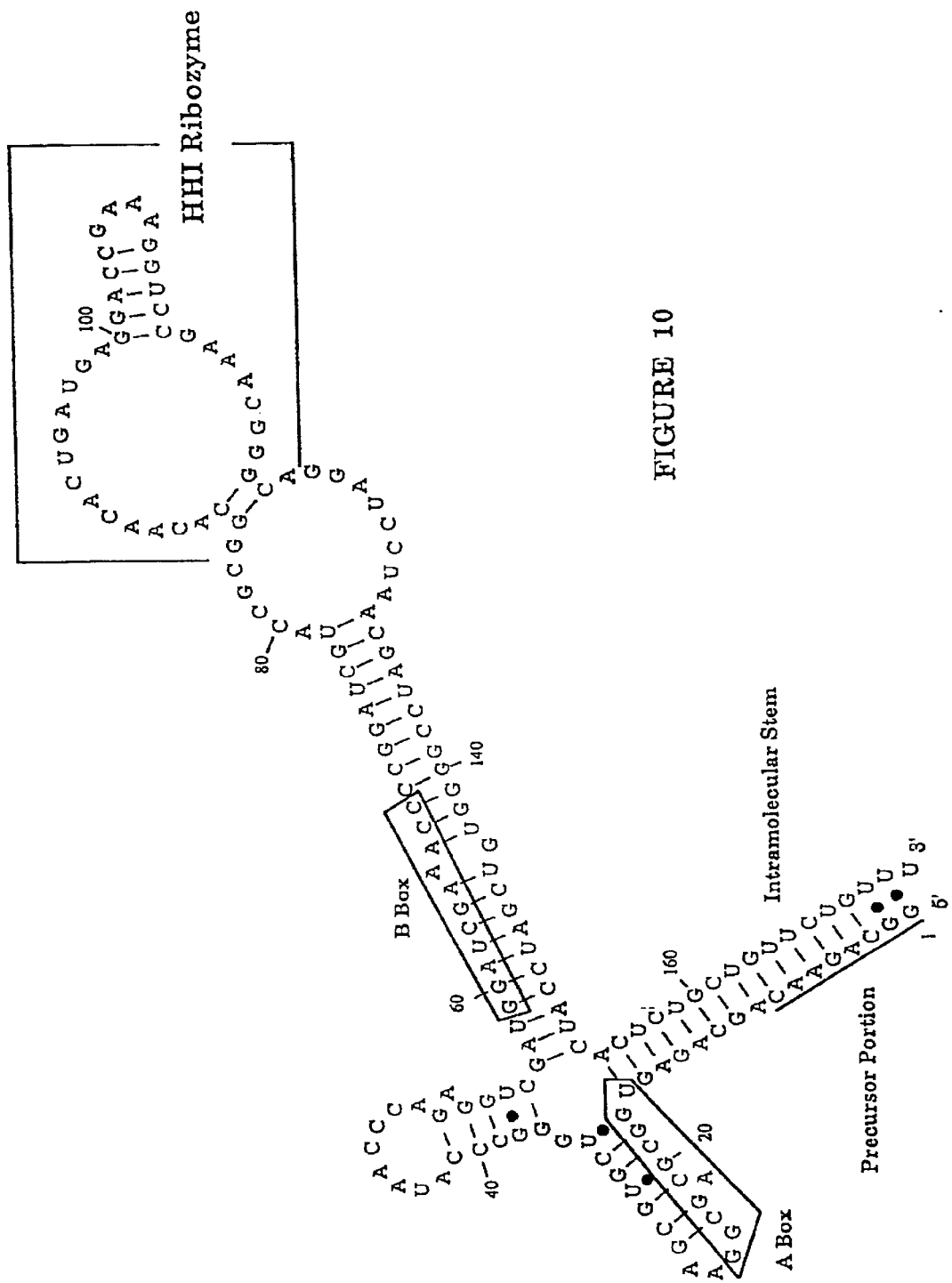

Variation in the ribozyme expression levels among cells making up the bulk population was determined by generating several clonal cell lines from the bulk S35 transduced CEM line (*Curr. Protocols Mol. Biol.* 1992, ed. Ausubel et al., Wiley & Sons, NY) and the ribozyme expression and activity levels in the individual clones were measured (FIG. 6). All the individual clones were found to express active ribozyme. The ribozyme activity detected from each clone correlated well with the relative amounts of ribozyme observed by Northern analysis. Steady state ribozyme levels among the clones ranged from approximately 1,000 molecules per cell in clone G to 11,000 molecules per cell in clone H (FIG. 6A). The mean accumulation among the clones, calculated by averaging the ribozyme levels of the clones, exactly equaled the level measured in the parent bulk population. This suggests that the individual clones are representative of the variation present in the bulk population.

The fact that all 14 clones were found to express ribozyme indicate that the percentage of cells in the bulk population expressing ribozyme is also very high. In addition, the lowest level of expression in the clones was still more than 10-fold that seen in bulk cells transduced with the original Δ3-5 vector. Therefore, the S35 gene unit should be much more effective in a gene therapy setting in which bulk cells are removed, transduced and then reintroduced back into a patient.

EXAMPLE 6

Stability

Finally, the bulk S35-transduced line, resistant to G418, was propogated for a period of 3 months (in the absence of G418) to determine if ribozyme expression was stable over extended periods of time. This situation mimicks that found in the clinic in which bulk cells are transduced and then reintroduced into the patient and allowed to propogate. There was a modest 30% reduction of ribozyme expression after 3 months. This difference probably arose from cells with varying amount of ribozyme expression and exhibiting different growth rates in the culture becoming slightly more prevalent in the culture. However, ribozyme expression is apparently stable for at least this period of time.

EXAMPLE 7

Design and Construction of TRZ-tRNA Chimera

A transcription unit, termed TRZ, is designed that contains the S35 motif (FIG. 16). A desired RNA (e.g. ribozyme) can-be inserted into the indicated region of TRZ tRNA chimera. This construct might provide additional stability to the desired RNA. TRZ-A and TRZ-B are non-limiting examples of the TRZ-tRNA chimera.

Figure 17:
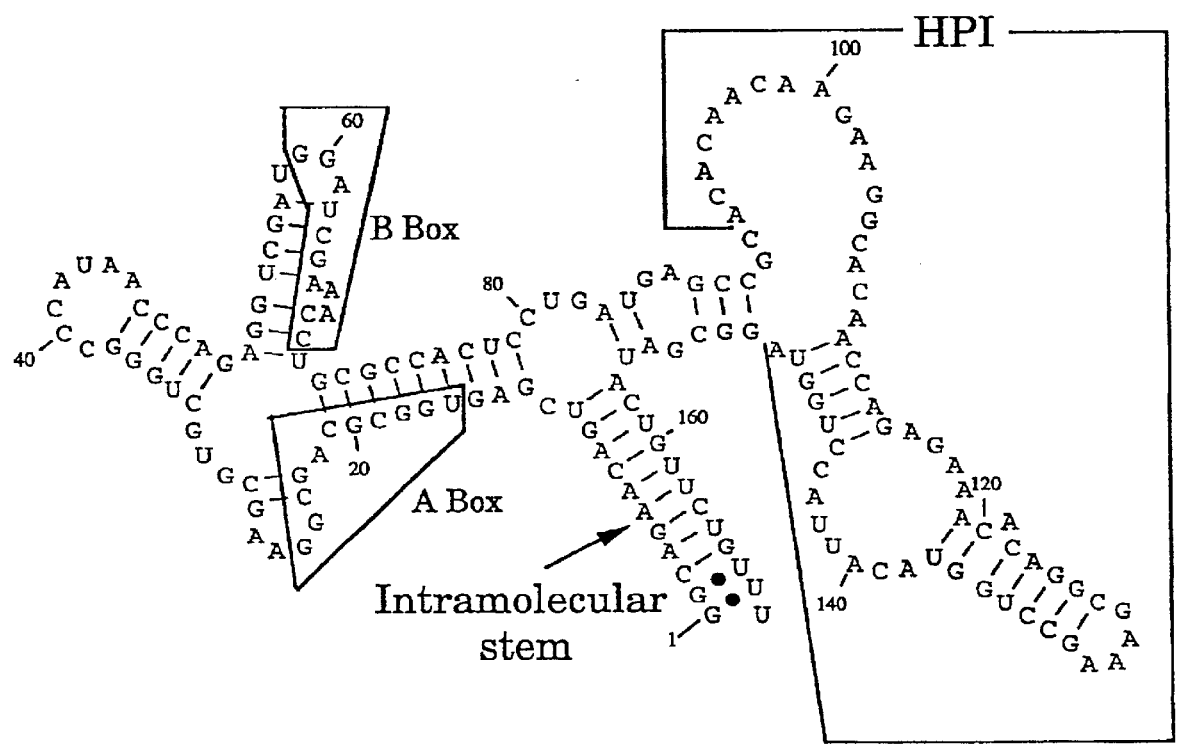

Referring to FIG. 17, a hammerhead ribozyme targeted to site I (HHITRZ-A; FIG. 17A) and a hairpin ribozyme (HPITRZ-A; FIG. 17B), also targeted to site I, is cloned individually into the indicated region of TRZ tRNA chimera. The resulting ribozyme transcripts retain full RNA cleavage activity (see for example FIG. 18). Applicant has shown that efficient expression of these TRZ tRNA chimera can be achieved in mammalian cells.

Besides ribozymes, desired RNAs like antisense, therapeutic editing RNAs, decoys, can be readily inserted into the indicated region of TRZ-tRNA chimera to achieve therapeutic levels of RNA expression in mammalian cells.

EXAMPLE 8

Design and Construction of U6-S35 Chimera

Figure 1:
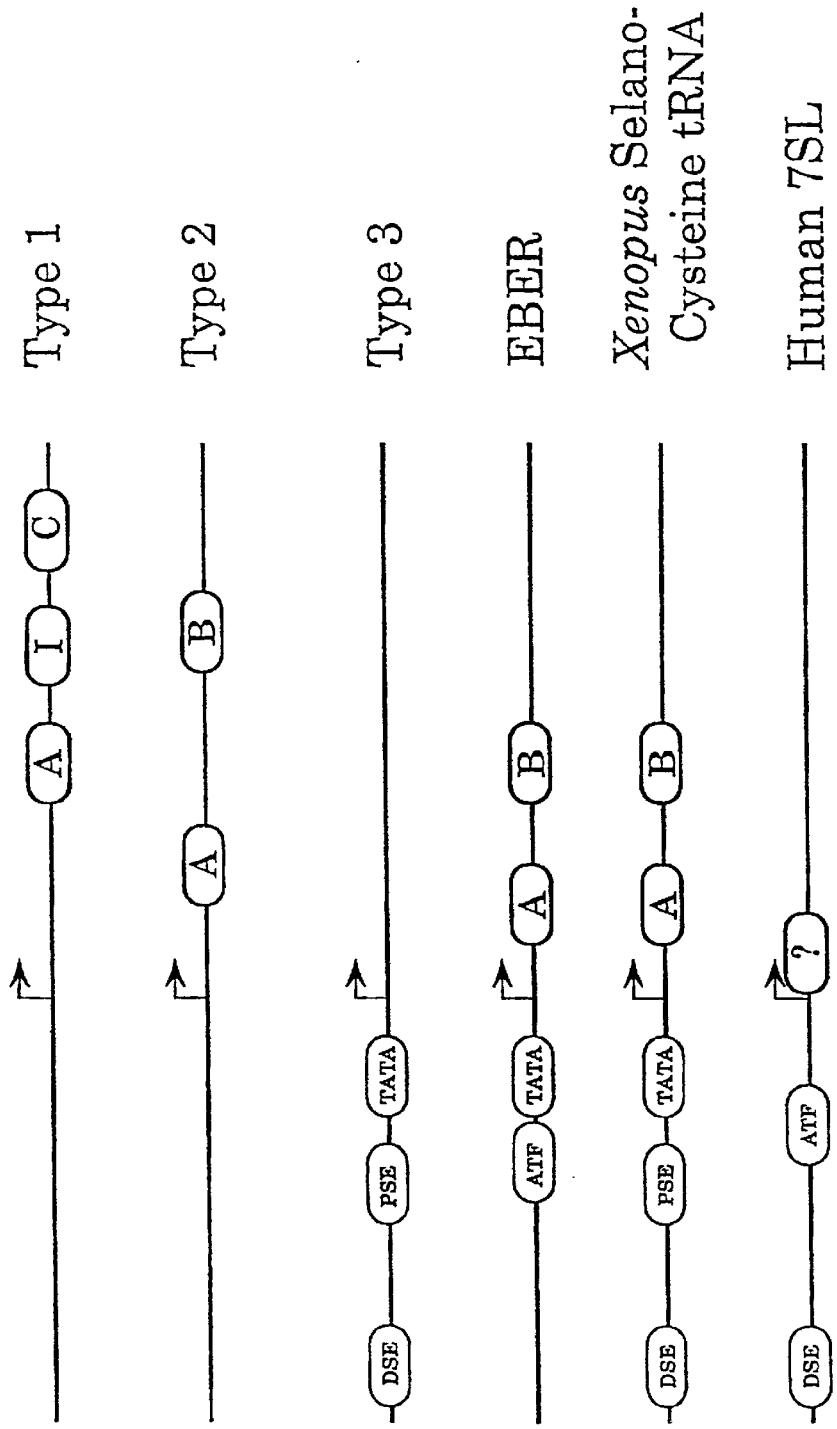

A transcription unit, termed U6-S35, is designed that contains the characteristic intramolecular stem of a S35 motif (see FIG. 13). As shown in FIG. 19, 20 and 21 a desired RNA (e.g. ribozyme) can be inserted into the indicated region of U6-S35 chimera. This construct is under the control of a type 3 pol III promoter, such as a mammalian U6 small nuclear RNA (snRNA) promoter (see FIG. 1). U6-S35-HHI and U6-S35-HHII are non-limiting examples of the U6-S35 chimera.

As a non-limiting example, applicant has constructed a stable, active ribozyme RNA driven from a eukaryotic U6 promoter (FIG. 20). For stability, applicant incorporated a S35 motif as described in FIG. 13 and FIG. 19. A ribozyme sequence is inserted at the top of the stem, such that the ribozyme is separated from the S35 motif by an unstructured spacer sequence (FIG. 19, 20, 21). The spacer sequence can be customized for each desired RNA sequence. U6-S35 chimera is meant to be a non-limiting example and those skilled in the art will recognize that the structure disclosed in the FIGS. 19, 20 and 21 can be driven by any of the known RNA polymerase promoters and are within the scope of this invention. All that is necessary is for the 5' region of a transcript to interact with its 3' region to form a stable intramolecular structure (S35 motif) and that the S35 motif is separated from the desired RNA by a stretch of unstructured spacer sequence. The spacer sequence appears to improve the effectiveness of the desired RNA.

By "unstructured" is meant lack of a secondary and tertiary structure such as lack of any stable base-paired structure within the sequence itself, and preferably with other sequences in the attached RNA.

By "spacer sequence" is meant any unstructured RNA sequence that separates the S35 domain from the desired RNA. The spacer sequence can be greater than or equal to one nucleotide.

In vitro Catalytic Activity of U6-S35-Ribozyme Chimeras:

U6-S35-HHI ribozyme RNA was synthesized using T7 RNA polymerase. HHI RNA was chemically synthesized using RNA phosphoramidite chemistry as described in Wincott et al., 1995 Nucleic Acids Res. (in press). The ribozyme RNAs were gel-purified and the purified ribozyme RNAs were heated to 55° C. for 5 min. Target RNA used was −650 nucleotide long. Internally-$^{32}$P-labeled target RNA was prepared as described above. The target RNA was pre-heated to 37° C. in 50 mM Tris.HCl, 10 mM MgCl$_2$ and then mixed at time zero with the ribozyme RNAs (to give 200 nM final concentration of ribozyme). At appropriate times an aliquot was removed and the reaction was stopped by dilution in 95% formamide. Samples were resolved on a denaturing urea-polyacrylamide gel and products were quantitated on a phospholmager®.

As shown in FIG. 22, the U6-S35-HHI ribozyme chimera cleaved its target RNA as efficiently as a chemically synthesized HHI ribozyme. In fact, it appears that the U6-S35-HHI ribozyme chimera may be more efficient than the synthetic ribozyme.

Accumulation of U6-S35-ribozyme transcripts

An Actinomycin D assay was used to measure accumulation of the transcript in mammalian cells. Cells were transfected overnight with plasmids encoding the appropriate transcription units (2 μg DNA/well of 6 well plate) using calcium phosphate precipitation method (Maniatis et al., 1982 Molecular Cloning Cold Spring Harbor Laboratory Press, NY). After the overnight transfection, media was replaced and the cells were incubated an additional 24 hours. Cells were then incubated in media containing 5 μg/ml Actinomycin D. At the times-indicated, cells were lysed in guanidinium isothiocyanate, and total RNA was purified by phenol/chloroform extraction and isopropanol precipitation as described by Chomczynski and Sacchi, 1987 Anal. Biochem., 162, 156. RNA was analyzed by northen blot analysis and the levels of specific RNAs were radioanalyticaly quantitated on a phospholmager®. The level of RNA at time zero was set to be 100%.

As shown in FIG. 23, the U6-S35-HHII ribozyme shown in FIG. 21 is fairly stable in 293 mammalian cells with an approximate half-life of about 2 hours.

EXAMPLE 9

Design and Construction of VA1-S35 Chimera

Referring to FIG. 25A, In order to express ribozymes from a VAI promoter, applicant has constructed a transcription unit consisting of a wild type VA1 sequence with two modifications: a "S35-like" motif extends from a loop in the central domain (FIG. 24); the 3' terminus is changed such that there is a more complete interaction between the 5' and the 3' region of the transcript (specifically, an "A-C" bulge is changed to an "A-U base pair and the termination sequence is part of the stem of S35 motif.

Accumulation of VA 1-S35-ribozyme transcripts

An Actinomycin D assay was used to measure accumulation of the transcript in mammalian cells as described above. As shown in FIG. 26, the VA1-S35-chimera, shown in FIG. 25A, has approximately 10-fold higher stability in 293 mammalian cells compared to VA1-chimera, shown in FIG. 25B that lacks the intramolecular S35 motif.

Besides ribozymes, desired RNAs like antisense, therapeutic editing RNAs, decoys, can be readily inserted into the indicated U6-S35 or VA1-S35 chimera to achieve therapeutic levels of RNA expression in mammalian cells.

Sequences listed in the Figures are meant to be non-limiting examples. Those skilled in the art will recognize that variants (mutations, insertions and deletions) of the above examples can be readily generated using techniques known in the art, are within the scope of the present invention.

Method for Administration and Use

References cited herein, as well as Draper WO 93/23569, 94/02495, WO 94/04609, and 93/11253 describe methods for use of vectors decribed herein, and are incorporated by reference herein. In particular these vectors are useful for administration of antisense and decoy RNA molecules.

Other embodiments are within the following claims.

What is claimed is:

1. A transcribed non-naturally occurring RNA molecule, comprising a desired RNA portion, wherein said desired RNA portion is present between a 3' region and a 5' region, wherein said 3' region and said 5' region from an intramolecular stem with each other comprising at least 8 base pairs, and wherein said RNA molecule is a chimeric tRNA.

2. A transcribed non-naturally occurring RNA molecule, comprising a desired RNA portion, wherein said desired RNA portion is present between a 3' region and a 5' region, wherein said 3' region and said 5' region form an intramolecular stem with each other comprising at least 8 base pairs, and wherein said RNA molecule is transcribed by a type 2 pol III promoter system, and wherein said RNA molecule has A and B boxes of a type 2 pol III promoter separated by between 0 and 300 bases.

3. The RNA molecule of claim 2, wherein said desired RNA portion is at the 3' end of said B box of said RNA molecule.

4. The RNA molecule of claim 2, wherein said desired RNA portion is in between said A and said B box of said RNA molecule.

5. The RNA molecule of claim 2, wherein said desired RNA portion includes the B box of said RNA molecule.

6. A RNA vector encoding a transcribed non-naturally occurring RNA molecule, comprising a desired RNA portion, wherein said desired RNA portion is present between a 3' region and a 5' region, wherein said 3' region and said 5' region form an intramolecular stem with each other comprising at least 8 base pairs.

7. A DNA vector encoding a transcribed non-naturally occurring RNA molecule, comprising a desired RNA portion, wherein said desired RNA portion is present between a 3' region and a 5' region, wherein said 3' region and said 5' region form an intramolecular stem with each other comprising at least 8 base pairs, and wherein the portions of the DNA vector encoding said RNA molecule unction as a RNA pol III promoter.

8. A cell in culture comprising a DNA vector encoding a transcribed non-naturally occurring RNA molecule, comprising a desired RNA portion, wherein said desired RNA portion is present between a 3' region and a 5' region, wherein said 3' region and said 5' region form an intramolecular stem with each other comprising at least 8 base pairs.

9. A cell in culture comprising the vector of claim 6.

10. A cell in culture comprising a transcribed non-naturally occurring RNA molecule, comprising a desired RNA portion, wherein said desired RNA portion is present between a 3' region and a 5' region, wherein said 3' region and said 5' region form an intramolecular stem with each other comprising at least 8 base pairs.

11. A method to provide a desired first RNA molecule in a cell in culture comprising introducing into said cell a second RNA molecule comprising a 5' region, a 3' region, and said desired first RNA molecule, wherein said 3' region and said 5' region form an intramolecular stem with each other comprising at least 8 base pairs, and wherein said desired first RNA molecule is present between the 3' region and the 5' region, under conditions suitable to provide the desired first RNA molecule in the cell.

12. The method of claim 11, wherein the introduction of the second RNA molecule comprises providing a vector encoding said second RNA molecule.

13. A transcribed non-naturally occurring RNA molecule comprising a desired RNA portion, wherein said desired RNA portion is present between a 3' region and a 5' region, wherein said 3' region and said 5' region form an intramolecular stem with each other comprising at least 8 base pairs, wherein said RNA molecule is a chimeric adenovirus VA1 RNA.

* * * * *

SEQUENCE LISTING

<160> NUMBER OF SEQ ID NOS: 22

<210> SEQ ID NO 1
<211> LENGTH: 88
<212> TYPE: RNA
<213> ORGANISM: Homo sapiens
<220> FEATURE:
<221> NAME/KEY: misc_feature
<222> LOCATION: (83)
<223> OTHER INFORMATION: n represents ribothymidine.
<221> NAME/KEY: misc_feature
<222> LOCATION: (86)..(88)
<223> OTHER INFORMATION: all n's represent ribothymidine.

<400> SEQUENCE: 1
ggcagaacag cagaguggcg cagcggaagc gugcugggcc cauaacccag aggucgaugg    60
aucgaaacca uccucugcua ggnccnnn                                      88

<210> SEQ ID NO 2
<211> LENGTH: 70
<212> TYPE: RNA
<213> ORGANISM: Artificial Sequence
<220> FEATURE:
<223> OTHER INFORMATION: Description of Artificial Sequence: a truncated
      version of tRNA.

<400> SEQUENCE: 2 ggcagaaccagcagaguggcgcagcggaagcgugcugggcccauaacccagaggucgaug       60 gaucgaaacc                                                          70

<210> SEQ ID NO 3
<211> LENGTH: 108
<212> TYPE: RNA
<213> ORGANISM: Artificial Sequence
<220> FEATURE:
<223> OTHER INFORMATION: Description of Artificial Sequence: S35 tRNA
      Chimera (S35).

<400> SEQUENCE: 3
ggcagaacag cagaguggcg cagcggaagc gugcugggcc cauaacccag aggucgaugg    60
aucgaaaccc cggaucguac cgcggggauc cacucugcug uucuguuu               108

<210> SEQ ID NO 4
<211> LENGTH: 146
<212> TYPE: RNA
<213> ORGANISM: Artificial Sequence
<220> FEATURE:
<223> OTHER INFORMATION: Description of Artificial Sequence: S35
      Ribozyme Chimera (HHIS35).

<400> SEQUENCE: 4
ggcagaacag cagaguggcg cagcggaagc gugcugggcc cauaacccag aggucgaugg    60
aucgaaaccc cggaucguac cgcggcacaa cacugaugag gaccgaaagg uccgaaacgg   120
gcaggaucca cucugcuguu cuguuu                                       146

<210> SEQ ID NO 5
<211> LENGTH: 133
<212> TYPE: RNA
<213> ORGANISM: Artificial Sequence
<220> FEATURE:
<223> OTHER INFORMATION: Description of Artificial Sequence: S35 Plus
      tRNA Chimera (S35 Plus).

```
<400> SEQUENCE: 5
ggcagaacag cagaguggcg cagcggaagc gugcugggcc cauaacccag aggucgaugg      60
aucgaaaccc cggaucguac cgcggggauc cuaacgaucc gggguqucga uccaucacuc     120 ugcuguucug uuu                                                       133

<210> SEQ ID NO 6
<211> LENGTH: 171
<212> TYPE: RNA
<213> ORGANISM: Artificial Sequence
<220> FEATURE:
<223> OTHER INFORMATION: Description of Artificial Sequence: S35 Plus
      Ribozyme Chimera (HHIS35 Plus).

<400> SEQUENCE: 6
ggcagaacag cagaguggcg cagcggaagc gugcugggcc cauaacccag aggucgaugg      60
aucgaaaccc cggaucguac cgcggcacaa cacugaugag gaccgaaagg uccgaaacgg     120
gcaggauccu aacgauccgg ggugucgauc caucacucug cguucuguu u              171

<210> SEQ ID NO 7
<211> LENGTH: 11
<212> TYPE: RNA
<213> ORGANISM: Artificial Sequence
<220> FEATURE:
<223> OTHER INFORMATION: Description of Artificial Sequence: A BOX
      consensus sequence.
<221> NAME/KEY: misc_feature
<222> LOCATION: (5)..(6)
<223> OTHER INFORMATION: each n represents any one of a, c, g, or u.

<400> SEQUENCE: 7
urgcnnagyg g                                                          11

<210> SEQ ID NO 8
<211> LENGTH: 11
<212> TYPE: RNA
<213> ORGANISM: Artificial Sequence
<220> FEATURE:
<223> OTHER INFORMATION: Description of Artificial Sequence: B BOX
      consensus sequence.
<221> NAME/KEY: misc_feature
<222> LOCATION: (8)
<223> OTHER INFORMATION: n represents any one of a, c, g, or u.

<400> SEQUENCE: 8
gguucganuc c                                                          11

<210> SEQ ID NO 9
<211> LENGTH: 129
<212> TYPE: RNA
<213> ORGANISM: Artificial Sequence
<220> FEATURE:
<223> OTHER INFORMATION: Description of Artificial Sequence: 5T tRNA
      Chimera (5T).

<400> SEQUENCE: 9
ggcagaacag cagaguggcg cagcggaagc gugcugggcc cauaacccag aggucgaugg      60
aucgaaacca uccucugcug uucugccgcg gcgaaagccg caaacacaca aaaacccccca   120 aaccccuuu                                                            129

<210> SEQ ID NO 10
<211> LENGTH: 167
<212> TYPE: RNA
<213> ORGANISM: Artificial Sequence
```

-continued

```
<220> FEATURE:
<223> OTHER INFORMATION: Description of Artificial Sequence: 5T Ribozyme
      Chimera (HHI5T).

<400> SEQUENCE: 10
ggcagaacag cagaguggcg cagcggaagc gugcugggcc cauaacccag aggucgaugg    60
aucgaaacca uccucugcug uucugccgcg gcgaaagccg caaacacaac acugaugagg   120
accgaaaggu ccgaaacggg cacacacaaa aacggcgaaa gccguuu                167

<210> SEQ ID NO 11
<211> LENGTH: 112
<212> TYPE: RNA
<213> ORGANISM: Artificial Sequence
<220> FEATURE:
<223> OTHER INFORMATION: Description of Artificial Sequence: TRZ-A tRNA
      Chimera.

<400> SEQUENCE: 11
ggcagaacag ucgaguggcg cagcggaagc gugcugggcc cauaacccag aggucgaugg    60
aucgaacacu gcgccaccucc ugaugagccg caaaggcgau acguucugu uu           112

<210> SEQ ID NO 12
<211> LENGTH: 112
<212> TYPE: RNA
<213> ORGANISM: Artificial Sequence
<220> FEATURE:
<223> OTHER INFORMATION: Description of Artificial Sequence: TRZ-B tRNA
      Chimera.

<400> SEQUENCE: 12
ggcagaacag ucgaguggcg cagcggaagc gugcugggcc caraacccag aggucgaugg    60
aucgaacacu gcgccacuca aaaaaagccg caaaggcgau acguucugu uu            112

<210> SEQ ID NO 13
<211> LENGTH: 148
<212> TYPE: RNA
<213> ORGANISM: Artificial Sequence
<220> FEATURE:
<223> OTHER INFORMATION: Description of Artificial Sequence: HHITRZ-A
      Ribozyme Chimera.

<400> SEQUENCE: 13
ggcagaacag ucgaguggcg cagcggaagc gugcugggcc cauaacccag aggucgaugg    60
aucgaacacu gcgccacucc ugaugagccg cacacaacac ugaugagccg aaaggcgaaa   120
cgggcacaca ggcgauacug uucuguuu                                     148

<210> SEQ ID NO 14
<211> LENGTH: 169
<212> TYPE: RNA
<213> ORGANISM: Artificial Sequence
<220> FEATURE:
<223> OTHER INFORMATION: Description of Artificial Sequence: HPITRZ-A
      Ribozyme Chimera.

<400> SEQUENCE: 14
ggcagaacag ucgaguggcg cagcggaagc gugcuugggc ccauaaccca gaggucgaug    60
gaucgaacac ugcgccacuc cugaugagcc gcacacaaca agaaggcaca accagagaaa  120
cacaggcgaa agccugguac auuaccuggu aggcgauacu guucuguuu              169

<210> SEQ ID NO 15
<211> LENGTH: 64
```

```
<212> TYPE: RNA
<213> ORGANISM: Artificial Sequence
<220> FEATURE:
<223> OTHER INFORMATION: Description of Artificial Sequence: a U6-S35
      chimera.
<221> NAME/KEY: unsure
<222> LOCATION: (1)..(64)
<223> OTHER INFORMATION: all n's represent ribothymidine.

<400> SEQUENCE: 15
gggcacncga anncaagcac aaacaaaaan aaaccaccaa acaaagcnng agnncgagng      60 nnnn                                                                  64

<210> SEQ ID NO 16
<211> LENGTH: 104
<212> TYPE: RNA
<213> ORGANISM: Artificial Sequence
<220> FEATURE:
<223> OTHER INFORMATION: Description of Artificial Sequence:  a U6-S35
      ribozyme chimera containing a hammerhead ribozyme
      targeted to site I (HHI).
<221> NAME/KEY: unsure
<222> LOCATION: (1)..(104)
<223> OTHER INFORMATION: all n's represent ribothymidine.

<400> SEQUENCE: 16
gggcacncga anncaagcac aaacaaaaaa cacaacacng angagccgaa aggcgaaacg      60
ggcacacana aaaccaccaa acaaagcnng agnncgagng nnnn                     104

<210> SEQ ID NO 17
<211> LENGTH: 102
<212> TYPE: RNA
<213> ORGANISM: Artificial Sequence
<220> FEATURE:
<223> OTHER INFORMATION: Description of Artificial Sequence: a
      U6-S35-ribozyme chimera containing a hammerhead
      ribozyme targeted to site II (HHII).

<400> SEQUENCE: 17
gggcacucga auucaagcac aaacacaaca auuucuuccu gaugagccga aaggcgaaaa      60
aaccgaacca cacaacaaac aaagcuugag uucgaguguu uu                       102

<210> SEQ ID NO 18
<211> LENGTH: 161
<212> TYPE: RNA
<213> ORGANISM: Adenovirus VA1 RNA.

<400> SEQUENCE: 18
uuucccgggc acucuuccgu ggucuggugg auaaauucgc aagggauauca uggcggacga     60 ccgggguucg aaccccggau cccggccguc cgccgugauc caugcgguua ccgcccgcgu    120
gucgaaccca ggugugcgac gucagacaac gggggagcgc u                        161

<210> SEQ ID NO 19
<211> LENGTH: 175
<212> TYPE: RNA
<213> ORGANISM: Artificial Sequence
<220> FEATURE:
<223> OTHER INFORMATION: Description of Artificial Sequence: VA1-S35
      Chimera.

<400> SEQUENCE: 19
gggcacucuu ccguggucug guagauaaau ucgcaagggu aucauggcgg acgaccgggg     60 uucgaaccccc ggauccggcc guccgccgug auccaugcgg uuaccgcgaa uucaagcgaa   120
```

-continued

```
agcuugaauu cgcgguaacc cagguguqcg agcucagaca acgggggagu guuuu          175

<210> SEQ ID NO 20
<211> LENGTH: 72
<212> TYPE: RNA
<213> ORGANISM: Artificial Sequence
<220> FEATURE:
<223> OTHER INFORMATION: Description of Artificial Sequence: VA1
      Chimera.

<400> SEQUENCE: 20
gggcaccucu uccguggucu gguagauuaa auucgcaagg guaucauggc ggacgaccgg      60
gguucgaacc cc                                                          72

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide encoding the S35 insert.

<400> SEQUENCE: 21
gatccactct gctgttctgt ttttga                                           26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide encoding the S35 insert.

<400> SEQUENCE: 22
cgcgtcaaaa acagaacagc agagtg                                           26
```